US010089413B2

(12) United States Patent
Wirx-Speetjens et al.

(10) Patent No.: US 10,089,413 B2
(45) Date of Patent: Oct. 2, 2018

(54) SYSTEMS AND METHODS FOR DESIGNING AND GENERATING DEVICES USING ACCURACY MAPS AND STABILITY ANALYSIS

(71) Applicant: Materialise NV, Leuven (BE)

(72) Inventors: Roel Wirx-Speetjens, Boortmeerbeek (BE); Joyce Van den Broeck, Kessel-Lo (BE); Michel Janssens, Grez-Doiceau (BE)

(73) Assignee: Materialise NV, Leuven (BE)

( * ) Notice: Subject to any disclaimer, the term of this patent is extended or adjusted under 35 U.S.C. 154(b) by 831 days.

(21) Appl. No.: 13/724,404

(22) Filed: Dec. 21, 2012

(65) Prior Publication Data

US 2013/0166256 A1    Jun. 27, 2013

Related U.S. Application Data

(60) Provisional application No. 61/579,927, filed on Dec. 23, 2011, provisional application No. 61/725,915, filed on Nov. 13, 2012.

(51) Int. Cl.
| | | |
|---|---|---|
| *G06F 17/50* | (2006.01) | |
| *B33Y 50/00* | (2015.01) | |
| *A61B 34/10* | (2016.01) | |

(52) U.S. Cl.
CPC ........ *G06F 17/50* (2013.01); *A61B 2034/105* (2016.02); *A61B 2034/108* (2016.02); *B33Y 50/00* (2014.12)

(58) Field of Classification Search
None
See application file for complete search history.

(56) References Cited

U.S. PATENT DOCUMENTS

| 5,141,680 A | 8/1992 | Almquist et al. |
| 5,192,539 A | 3/1993 | Van Der Marel et al. |
| (Continued) | | |

FOREIGN PATENT DOCUMENTS

WO    WO 2012/150336    11/2012

OTHER PUBLICATIONS

"Indicators of dynamic stability in transtibial prosthesis users", Kendall et al. © 2010 Elsevier B.V.*

(Continued)

*Primary Examiner* — Aniss Chad
*Assistant Examiner* — Nithya J Moll
(74) *Attorney, Agent, or Firm* — Patterson & Sheridan LLP

(57) ABSTRACT

Systems and methods for designing and generating a device using accuracy maps and stability analysis are disclosed herein. In some aspects, the systems and methods described relate to an apparatus for designing a device. The apparatus includes a processor configured to generate a three-dimensional model of a physical object and determine whether the three-dimensional model satisfies an accuracy threshold based on an accuracy map. The processor is further configured generate a simulated representation of the device, determine whether the simulated representation of the device satisfies a stability threshold, simulate a fit of the device on the three-dimensional model if the simulated representation of the device satisfies the stability threshold, and determine whether the simulated fit of the device on the three-dimensional model is within a tolerance threshold. The processor is further configured to generate an approved design of the device if the simulated fit is within the tolerance threshold.

26 Claims, 12 Drawing Sheets

(56) References Cited

U.S. PATENT DOCUMENTS

| | | |
|---|---|---|
| 7,227,981 B1* | 6/2007 | Fleute et al. .................. 382/132 |
| 7,584,080 B2* | 9/2009 | Taylor et al. ...................... 703/2 |
| 8,055,046 B2 | 11/2011 | Feilkas et al. |
| 8,112,142 B2* | 2/2012 | Alexander et al. ........... 600/407 |
| 2005/0015003 A1 | 1/2005 | Lachner et al. |
| 2007/0066917 A1* | 3/2007 | Hodorek ................ A61B 90/36 600/595 |
| 2010/0161076 A1 | 6/2010 | Pallari |
| 2011/0093108 A1 | 4/2011 | Ashby et al. |
| 2012/0039525 A1* | 2/2012 | Tian ........................ G06T 5/005 382/154 |

OTHER PUBLICATIONS

Harada, Yoshitada, et al. "Anatomically designed prosthesis without cement for the treatment of osteoarthritis due to developmental dysplasia of the hip: 6-to 13-year follow-up study." Journal of Orthopaedic Science 12.2 (2007): 127-133.*

Besl, Paul J. and Neil D. McKay, "A Method for Registration of 3-D Shapes" *IEEE Transactions on Pattern Analysis and Machine Intelligence* (1992) 14(2): 239-256.

Lin, et al., "A Stiffness-Based Quality Measure for Compliant Grasps and Fixtures" *IEEE Transactions on Robotics and Automation* (2000) 16(6): 675-688.

Lorense, William E. and Harvey E. Cline, "Marching Cubes: A High Resolution 3D Surface Construction Algorithm" *Computer Graphics* (1987) 21(4): 163-169.

Rusinkiewicz, Szymon and Marc Levoy, "Efficient Variants of the ICP Algorithm" Stanford University, *Proc. 3DIM* (2001): 1-8.

Van den Broeck, et al., "Preoperative Analysis of the Stability of a Patient-Specific Surgical Guide: A Case Study" *10th International Symposium: Computer Methods in Biomechanics and Biomedical Engineering 2012*, Hotel Berlin, Berlin, Germany, Apr. 11-14, 2012.

Zheng, et al., "A 2D/3D correspondence building method for reconstruction of a patient-specific 3D bone surface model using point distribution models and calibrated X-ray images" *Medical Image Analysis* (2009) 13: 883-899.

* cited by examiner

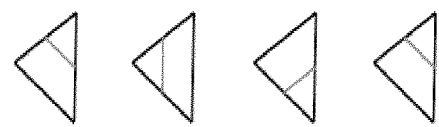
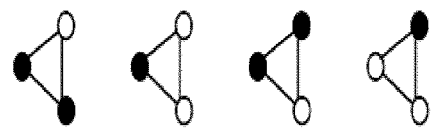
Figure 10
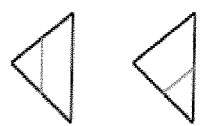
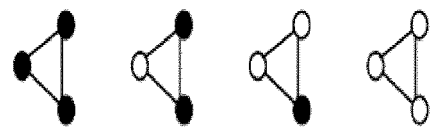

SYSTEMS AND METHODS FOR DESIGNING AND GENERATING DEVICES USING ACCURACY MAPS AND STABILITY ANALYSIS

PRIORITY

The present application the benefit of U.S. Provisional Patent Application No. 61/579,927, entitled "METHOD OF OBTAINING THREE DIMENSIONAL MODELS FROM PROJECTED IMAGES," filed Dec. 23, 2011, assigned to the assignee hereof and incorporated herein by reference in its entirety. The present application also claims the benefit of U.S. Provisional Patent Application No. 61/725,915, entitled "SYSTEMS AND METHODS FOR DESIGNING AND GENERATING DEVICES USING ACCURACY MAPS AND STABILITY ANALYSIS," filed Nov. 13, 2012, assigned to the assignee hereof and also incorporated herein by reference in its entirety.

BACKGROUND OF THE INVENTION

Field of the Invention

This invention relates to systems and methods for designing and generating devices or objects on a computer. More particularly, the invention relates to designing and generating devices or products on a computer using accuracy maps and stability analysis.

Description of the Related Technology

Object design and manufacture are used to create necessary tools for a number of different industries. For example, parts, tools, etc. may be designed and manufactured for use in all aspects of everyday life. The process of designing and manufacturing such objects, however, can be time intensive and expensive. For example, traditional manufacturing techniques may require designing and building a prototype, creating molds based on the design, drilling and cutting of components, and other time consuming and expensive techniques to create a single object. There may be economies of scale when making subsequent objects identical to the initially designed object as molds, etc. can be reused. However, for one off objects, no such economies of scale are gained.

Accordingly, traditional design and manufacturing techniques are ill suited for generating one off or customized objects, such as, surgical implants specifically designed for a patient, prototypes, etc. Processes such as additive manufacturing (e.g., 3-D printing), can overcome such limitations by reducing the time and cost of creating an object. Additive manufacturing can be defined as a group of techniques used to fabricate a tangible model of an object, such as using three-dimensional (3-D) computer aided design (CAD) data of the object.

Typically, additive manufacturing techniques start from a digital representation of the 3-D object to be formed. Generally, the digital representation is sliced into a series of cross-sectional layers that can be overlaid to form the object as a whole. An additive manufacturing apparatus uses this data for building the object on a layer-by-layer basis. Simulation models may be used along with reference data (e.g., 2-D data) to generate a 3-D digital representation of an object. The accuracy of the 3-D digital representation of the object may vary depending on the process used to obtain the digital representation. Various applications (e.g., machining, surgical, manufacturing, etc.) may require accurate and precise representations of objects in order to design usable products for use with those objects. Furthermore, it is desired that a product designed for use with an object is stable with regard to that object. Accordingly, improved systems and techniques are needed for designing and generating a device or product.

SUMMARY

Various implementations of systems, methods and devices within the scope of the appended claims each have several aspects, no single one of which is solely responsible for the desirable attributes described herein. Without limiting the scope of the appended claims, some prominent features are described herein.

Details of one or more implementations of the subject matter described in this specification are set forth in the accompanying drawings and the description below. Other features, aspects, and advantages will become apparent from the description, the drawings, and the claims. Note that the relative dimensions of the following figures may not be drawn to scale.

One aspect of the subject matter described in the disclosure provides an apparatus for designing a device. The apparatus comprises a processor configured to generate a three-dimensional model of a physical object and determine whether the three-dimensional model satisfies an accuracy threshold based on an accuracy map. The processor is further configured to generate a simulated representation of the device, determine whether the simulated representation of the device satisfies a stability threshold, simulate a fit of the device on the three-dimensional model if the simulated representation of the device satisfies the stability threshold, and determine whether the simulated fit of the device on the three-dimensional model is within a tolerance threshold. The processor is further configured to generate an approved design of the device if the simulated fit is within the tolerance threshold.

Another aspect of the subject matter described in the disclosure provides an implementation of a method of designing a device. The method comprises generating a three-dimensional model of a physical object and determining whether the three-dimensional model satisfies an accuracy threshold based on an accuracy map. The method further comprises generating a simulated representation of the device, determining whether the simulated representation of the device satisfies a stability threshold, simulating a fit of the device on the three-dimensional model if the simulated representation of the device satisfies the stability threshold, and determining whether the simulated fit of the device on the three-dimensional model is within a tolerance threshold. The method further comprises generating an approved design of the device if the simulated fit is within the tolerance threshold.

Yet another aspect of the subject matter described in the disclosure provides an apparatus for designing a device. The apparatus comprises means for generating a three-dimensional model of a physical object and means for determining whether the three-dimensional model satisfies an accuracy threshold based on an accuracy map. The apparatus further comprises means for generating a simulated representation of the device, means for determining whether the simulated representation of the device satisfies a stability threshold, means for simulating a fit of the device on the three-dimensional model if the simulated representation of the device satisfies the stability threshold, and means for determining whether the simulated fit of the device on the three-dimensional model is within a tolerance threshold. The apparatus further comprises means for generating an approved design of the device if the simulated fit is within the tolerance threshold.

Another aspect of the subject matter described in the disclosure provides an implementation of a computer program product. The computer program product comprises a computer-readable medium comprising code for generating a three-dimensional model of a physical object and code for determining whether the three-dimensional model satisfies an accuracy threshold based on an accuracy map. The computer program product further comprises code for generating a simulated representation of the device, code for determining whether the simulated representation of the device satisfies a stability threshold, code for simulating a fit of the device on the three-dimensional model if the simulated representation of the device satisfies the stability threshold, and code for determining whether the simulated fit of the device on the three-dimensional model is within a tolerance threshold. The computer program product further comprises code for generating an approved design of the device if the simulated fit is within the tolerance threshold.

BRIEF DESCRIPTION OF THE DRAWINGS

FIG. 10 illustrates a process of finding zero-curves of a real-valued function g.

DETAILED DESCRIPTION OF CERTAIN INVENTIVE EMBODIMENTS

Figure 1:
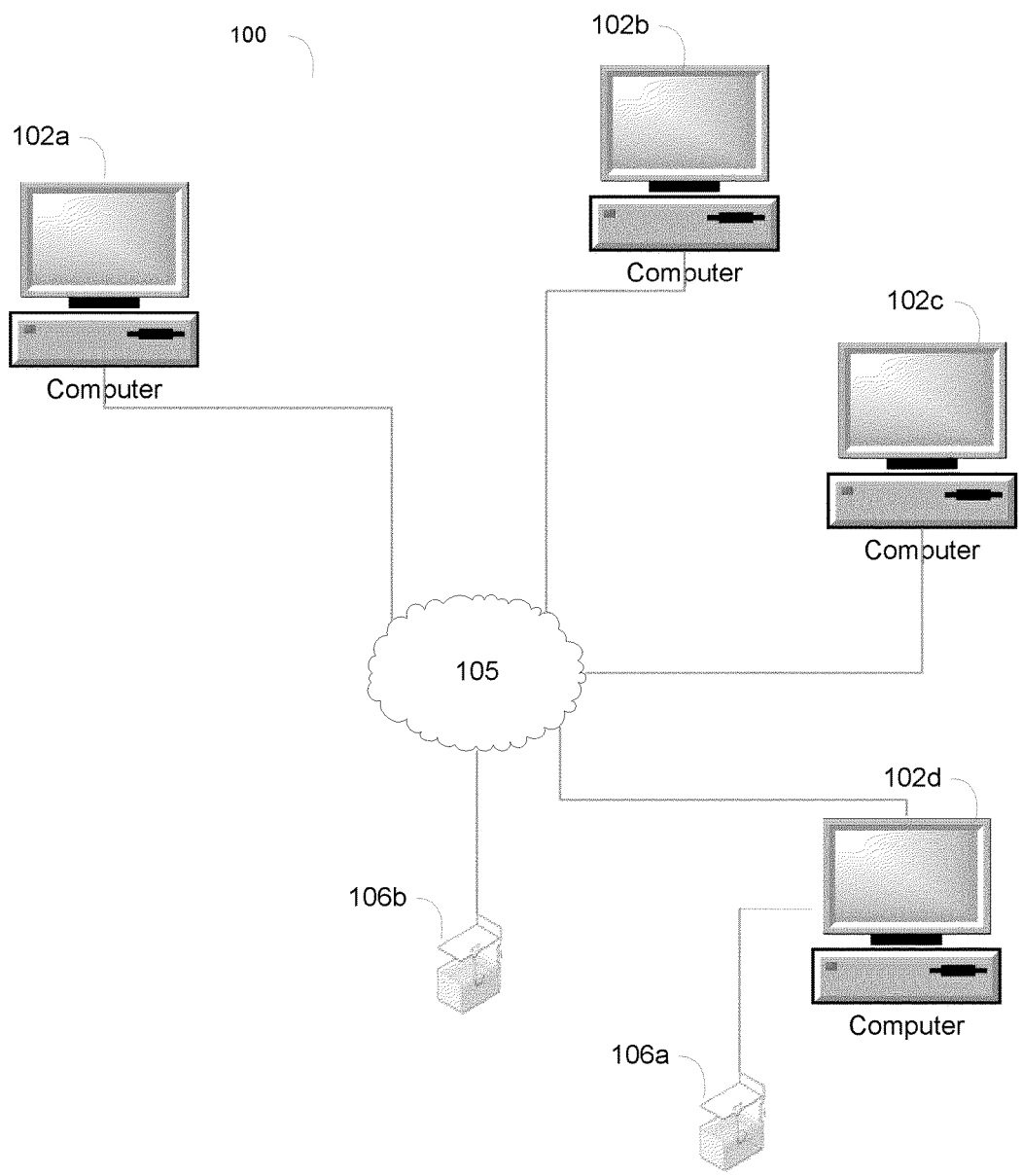
FIG. 1 depicts one example of a system for designing and manufacturing 3-D objects.

The following detailed description is directed to certain specific embodiments. However, the teachings herein can be applied in a multitude of different ways. In this description, reference is made to the drawings wherein like parts are designated with like numerals throughout.

The present invention will be described with respect to particular embodiments but the invention is not limited thereto but only by the claims.

As used herein, the singular forms "a", "an", and "the" include both singular and plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps. The terms "comprising", "comprises" and "comprised of" when referring to recited components, elements or method steps also include embodiments which "consist of" said recited components, elements or method steps.

Furthermore, the terms first, second, third and the like in the description and in the claims, are used for distinguishing between similar elements and not necessarily for describing a sequential or chronological order, unless specified. It is to be understood that the terms so used are interchangeable under appropriate circumstances and that the embodiments of the invention described herein are capable of operation in other sequences than described or illustrated herein.

Reference throughout this specification to "one embodiment," "an embodiment," "some aspects," "an aspect," or "one aspect" means that a particular feature, structure or characteristic described in connection with the embodiment or aspect is included in at least one embodiment of the present invention. Thus, appearances of the phrases "in one embodiment," "in an embodiment," "some aspects," "an aspect," or "one aspect" in various places throughout this specification are not necessarily all referring to the same embodiment or aspects, but may. Furthermore, the particular features, structures or characteristics may be combined in any suitable manner, as would be apparent to a person skilled in the art from this disclosure, in one or more embodiments or aspects. Furthermore, while some embodiments or aspects described herein include some but not other features included in other embodiments or aspects, combinations of features of different embodiments or aspects are meant to be within the scope of the invention, and form different embodiments or aspects, as would be understood by those in the art. For example, in the appended claims, any of the features of the claimed embodiments or aspects can be used in any combination.

In some aspects, 2-D or 3-D digital representations or models of an object may be created to provide a reference object from which to design products or devices for use with the object. For example, a digital representation of a patient's bone may be created in order to design a surgical guide, prosthetic device, and/or orthotic device for use with the patient's bone. In some aspects, 2-D information may be used to produce a digital representation of the 3-D object. A digital simulated representation of the product or device may be compared with the digital representation of the object in order to design the product or device to be used with the object. For example, a 2-D or 3-D model of the product or device may be compared with or fit to a 2-D or 3-D digital representation of an object (e.g., by registering or fitting the simulated representation or model on top of the digital representation of the object). Depending on the particular application (e.g., machining, surgical, etc.) for which the designed product or device applies, an accurate and precise digital representation or model of the object may be required in order to provide a usable product or device. Furthermore, the product or device should be stable with regard to the object for which it is designed.

Furthermore, imaging techniques such as X-ray radiography may be used for qualitative measurements and diagnostics. For example, X-rays may be used to determine whether a bone is broken or to see if a tumor is present in a patient. X-ray imaging techniques provide two dimensional (2-D) images, whereas other imaging technologies (e.g., computer tomography (CT) and magnetic resonance imaging (MRI)) may provide three dimensional (3-D) images. Imaging techniques using X-rays are valuable because X-rays are fast and easy to perform, and requires only limited imaging tools compared to other imaging techniques, such as those using CT or MRI. While several tools and options have been developed to improve the accuracy of X-ray imaging, using X-ray images as a digital representation of an object used for designing becomes difficult because X-ray images are projected images that only provide 2-D images.

Accordingly, systems and methods allow for designing and generating a device or product using accuracy maps and stability analysis. In some aspects, the device or product may be designed and generated for use with an object based on a 3-D model of the object generated from 2-D images. In some aspects, the designed device may be manufactured or generated through additive manufacturing.

While some aspects and/or embodiments described below provide specific examples including surgical or medical devices, tools, guides, etc., one of ordinary skill in the art would understand that the principles described herein apply equally to any other types of devices or products that may be manufactured (e.g., using additive manufacturing), including, but not limited to, machine equipment, sporting equipment, athletic gear, office equipment, etc.

In some aspects, a patient-specific device may be designed and generated using the accuracy maps and stability analysis described in detail below. The term "patient-specific" as used herein refers to surgical devices, tools, and/or guides that are designed starting from an individual patient's anatomy to provide a custom fit and/or function for the particular individual patient. The use of patient-specific devices, tools, or guides allows for improved or optimized surgical interventions, orthopedic structures, and/or kinematics for the patient.

A user (e.g., an engineer, designer, surgeon, physician, etc.) during pre-operative procedures may identify various regions of a body part (e.g., a bone) of a specific patient and may determine, based on the identified regions of the body part, an optimal design for a surgical device. Pre-operative procedures may include obtaining an image of a patient's body part prior to performing surgery. Digital patient-specific image information may be provided by any suitable means known in the art, such as, for example, an X-ray, a computer tomography (CT) scanner, a magnetic resonance imaging (MRI) scanner, an ultrasound scanner, etc. The pre-operative planning may include the construction of a three-dimensional (3-D) virtual model of a body part. In some aspects, construction of the 3-D virtual model may begin with scanning of a patient. For example, the scanning may include using a scanning technique that generates medical data, such as an X-ray, CT scan, MRI scan, or the like. In some aspects, the output of the scan may include a stack of two-dimensional (2-D) slices forming a 3-D data set. The output of the scan may be digitally imported into a computer program and may be converted using algorithms known in the field of image processing technology to produce a 3-D computer model of the body part. For example, the virtual 3-D model may be constructed from the data set using a computer program such as Mimics® as supplied by Materialise N.V., Leuven, Belgium. Once the 3-D volume of the body part, or a part thereof, is reconstructed, the user may define the preferred position, orientation, depth, and diameter of the various parts of the device that are needed for the surgery. Based on the determined surgical needs, the user may design, manufacture, and/or manipulate the device to meet the needs of the specific patient. Creation of an accurate, stable patient-specific device with respect to use in surgery is an important aspect in the successful design of the device.

FIG. 1 depicts one example of a system 100 for designing and manufacturing 3-D devices or product. The system 100 is configured to support the techniques described herein. For example, the system 100 may be configured to design and generate the device or product using accuracy maps and stability analysis, as described in further detail below. The system 100 includes one or more computers 102a-102-D, which can be, for example, any workstation, server, or other computing device capable of processing information. In some aspects, each of the computers 102a-102-D can be connected, by any suitable communications technology (e.g., an internet protocol), to a network 105 (e.g., the Internet). Accordingly, the computers 102a-102-D may transmit and receive information (e.g., software, digital representations of 3-D objects, commands or instructions to operate an additive manufacturing device, etc.) between each other via the network 105. The system 100 further includes one or more additive manufacturing devices (e.g., 3-D printers, etc.) 106a-106b. As shown the additive manufacturing device 106a is directly connected to a computer 102-D (and through computer 102-D connected to computers 102a-102c via the network 105) and additive manufacturing device 106b is connected to the computers 102a-102-D via the network 105. Accordingly, one of skill in the art will understand that an additive manufacturing device 106 may be directly connected to a computer 102, connected to a computer 102 via a network 105, and/or connected to a computer 102 via another computer 102 and the network 105.

It should be noted that though the system 100 is described with respect to a network and one or more computers, the techniques described herein also apply to a single computer 102, which may be directly connected to an additive manufacturing device 106.

Figure 2:
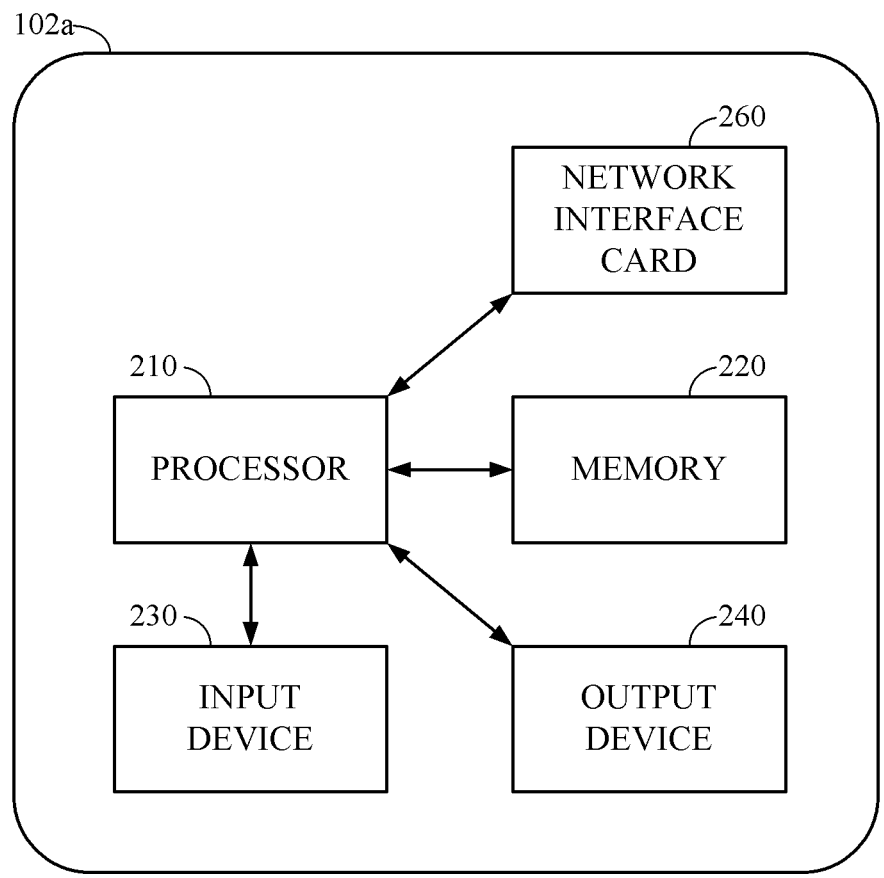
FIG. 2 illustrates a functional block diagram of one example of a computer of FIG. 1.

FIG. 2 illustrates a functional block diagram of one example of a computer of FIG. 1. The computer 102a includes a processor 210 in data communication with a memory 220, an input device 230, and an output device 240. In some embodiments, the processor is further in data communication with an optional network interface card 260. Although described separately, it is to be appreciated that functional blocks described with respect to the computer 102a need not be separate structural elements. For example, the processor 210 and memory 220 may be embodied in a single chip.

The processor 210 can be a general purpose processor, a digital signal processor (DSP), an application specific integrated circuit (ASIC), a field programmable gate array (FPGA) or other programmable logic device, discrete gate or transistor logic, discrete hardware components, or any suitable combination thereof designed to perform the functions described herein. A processor may also be implemented as a combination of computing devices, e.g., a combination of a DSP and a microprocessor, a plurality of microprocessors, one or more microprocessors in conjunction with a DSP core, or any other such configuration.

The processor 210 can be coupled, via one or more buses, to read information from or write information to memory 220. The processor may additionally, or in the alternative, contain memory, such as processor registers. The memory 220 can include processor cache, including a multi-level hierarchical cache in which different levels have different capacities and access speeds. The memory 220 can also include random access memory (RAM), other volatile storage devices, or non-volatile storage devices. The storage can include hard drives, optical discs, such as compact discs (CDs) or digital video discs (DVDs), flash memory, floppy discs, magnetic tape, and Zip drives.

The processor 210 also may be coupled to an input device 230 and an output device 240 for, respectively, receiving input from and providing output to a user of the computer 102a. Suitable input devices include, but are not limited to, a keyboard, a rollerball, buttons, keys, switches, a pointing device, a mouse, a joystick, a remote control, an infrared detector, a voice recognition system, a bar code reader, a scanner, a video camera (possibly coupled with video processing software to, e.g., detect hand gestures or facial gestures), a motion detector, a microphone (possibly coupled to audio processing software to, e.g., detect voice commands), or other device capable of transmitting information from a user to a computer. The input device can also be a touch screen associated with the display, in which case a user responds to prompts on the display by touching the screen. The user may enter textual information through the input device such as the keyboard or the touch-screen. Suitable output devices include, but are not limited to, visual output devices, including displays and printers, audio output devices, including speakers, headphones, earphones, and alarms, additive manufacturing devices, and haptic output devices.

The processor 210 further may be coupled to a network interface card 260. The network interface card 260 prepares data generated by the processor 210 for transmission via a network according to one or more data transmission protocols. The network interface card 260 also decodes data received via a network according to one or more data transmission protocols. The network interface card 260 can include a transmitter, receiver, or both. In other embodiments, the transmitter and receiver can be two separate components. The network interface card 260, can be embodied as a general purpose processor, a digital signal processor (DSP), an application specific integrated circuit (ASIC), a field programmable gate array (FPGA) or other programmable logic device, discrete gate or transistor logic, discrete hardware components, or any suitable combination thereof designed to perform the functions described herein.

Figure 3:
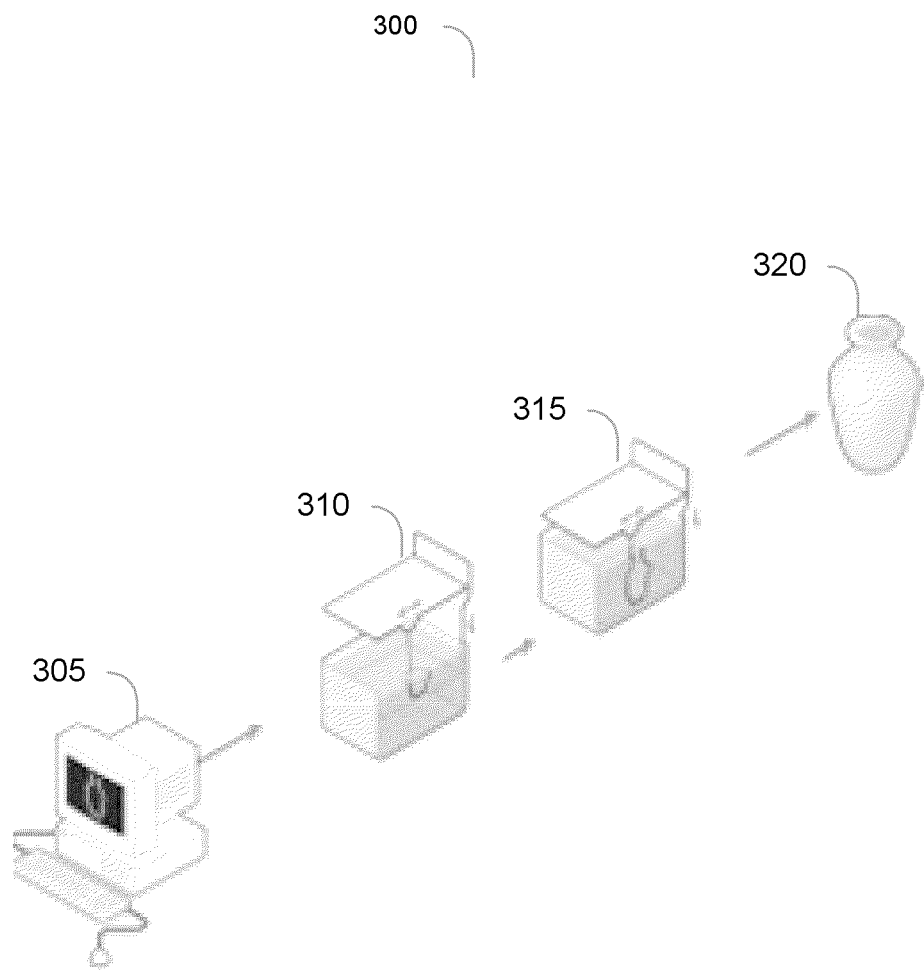
FIG. 3 illustrates a process for manufacturing a 3-D object.

FIG. 3 illustrates a process 300 for manufacturing a 3-D product or device. As shown, at a step 305, a digital representation of the device is designed using a computer, such as the computer 102a. For example, a 2-D representation of the device may be used to create a 3-D model of the device. As another example, 3-D data may be input to the computer 102a for aiding in designing the digital representation of the 3-D device. Continuing at a step 310, information is sent from the computer 102a to an additive manufacturing device, such as additive manufacturing device 106. At a step 315, the additive manufacturing device 106 begins manufacturing the 3-D device using suitable materials. Suitable materials include, but are not limited to polyurethane, acrylonitrile butadiene styrene (ABS), polycarbonate (PC), PC-ABS, polyamide, polyamide with additives such as glass or metal particles, methyl methacrylate-acrylonitrile-butadiene-styrene copolymer, resorbable materials such as polymer-ceramic composites, etc. Examples of commercially available materials are: DSM Somos® series of materials 7100, 8100, 9100, 9420, 10100, 11100, 12110, 14120 and 15100 from DSM Somos; ABSplus-P430, ABSi, ABS-ESD7, ABS-M30, ABS-M30i, PC-ABS, PC-ISO, PC, ULTEM 9085, PPSF and PPSU materials from Stratasys; Accura Plastic, DuraForm, CastForm, Laserform and VisiJet line of materials from 3-Systems; Aluminium, Cobal-tChrome and Stainless Steel materials; Maranging Steel; Nickel Alloy; Titanium; the PA line of materials, PrimeCast and PrimePart materials and Alumide and CarbonMide from EOS GmbH. Further, at a step 320, the 3-D device is generated.

Figure 4:
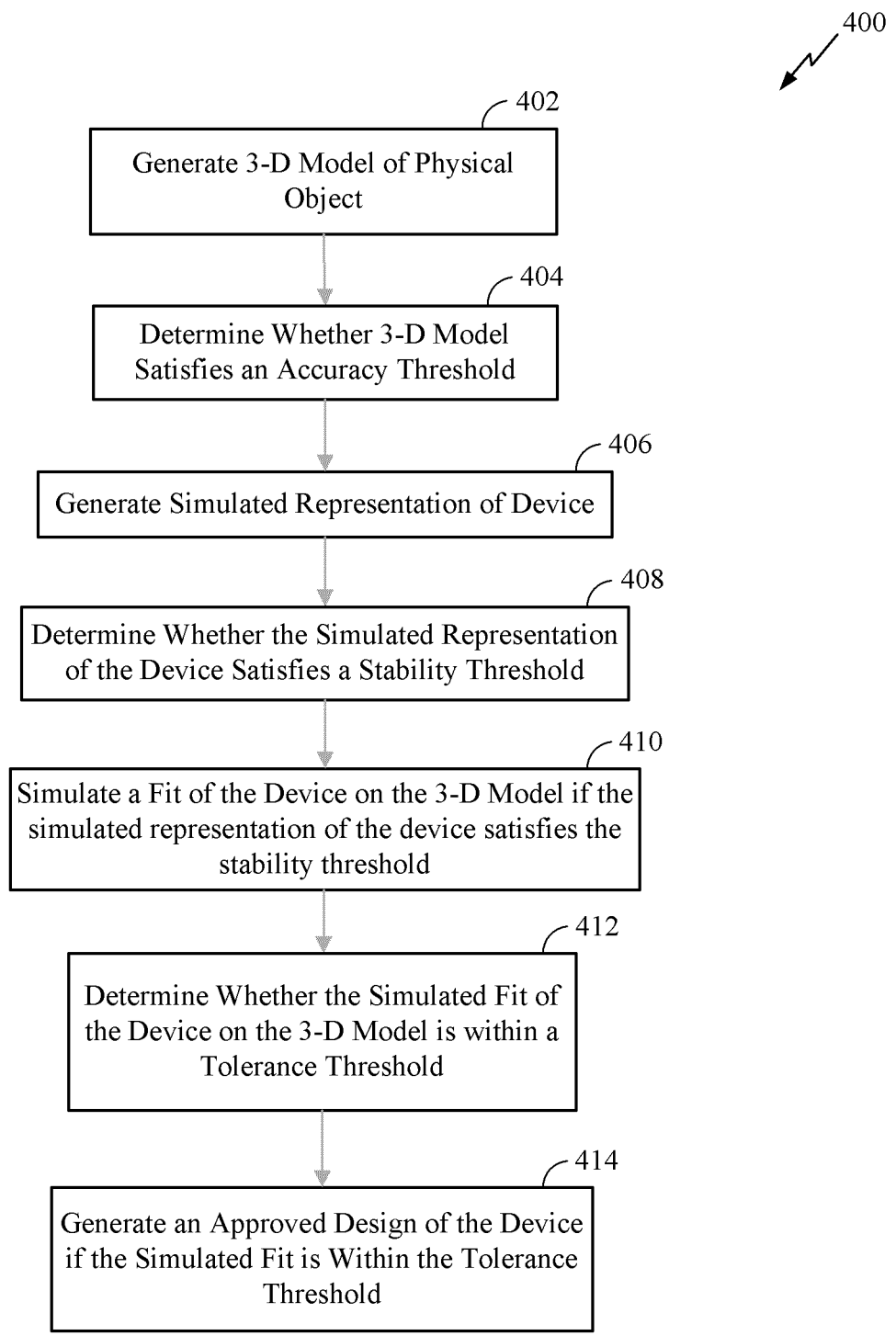
FIG. 4 illustrates a process for designing and generating a device using accuracy and stability analysis.

According to certain aspects, systems and methods allow for designing and generating a device or product using accuracy maps and stability analysis. Digital representations or models of an object may be generated to provide a reference object from which to design products or devices that may be used with the object. Accuracy maps and stability analysis may be used to aid in the design of these products or devices. FIG. 4 illustrates an example of a process 400 for designing a device. In some aspects, the process 400 may be implemented by various means, such as computer 102a using, for example, processor 210. At block 402, the process begins by generating a three-dimensional (3-D) model or digital representation of a physical object. In some aspects, the physical object may include a subject's or patient's region of interest, which may include any part of the subject or patient, such as a specific anatomical part of the subject or patient. The physical object, for example, may include a human body part, such as a bone (e.g., femur, humerus, spine, etc.), a leg, an arm, an ankle, etc. In some aspects, the 3-D model may be generated based on 2-D images of the physical object. For example, a simulated model relating to the object may be compared with 2-D images of the object in order to generate the 3-D model. As another example, a statistical shape model representing the physical object may be compared with or fit to an X-ray of the physical object (e.g., by registering the statistical shape model on top of the X-ray). In some aspects, the 3-D model may be generated based on 3-D imaging techniques (e.g., segmentation). In some aspects, the 3-D model may be based on 3-D reconstruction of computed tomography (CT) or magnetic resonance imaging (MRI) images. Further details regarding generation of a 3-D model of the physical object will be described below with reference to FIG. 5.

At block 404, the process continues by determining whether the 3-D model of the physical object satisfies an accuracy threshold, for example, based on an accuracy map. The accuracy threshold may be set by a user or may correspond to requirements and/or constraints of the particular application for which the device design applies. The accuracy threshold may be set to determine whether the 3-D model of the physical object is sufficiently accurate for the particular application. For example, the accuracy of a 3-D model of a patient's femur obtained by comparing a statistical shape model representing the femur to an X-ray of the patient's femur may be analyzed to determine if the 3-D model is sufficiently accurate for use in the design of a device or tool that is to be used with the femur (e.g., a surgical guiding tool). The accuracy of the 3-D model of the physical object may be determined based on an accuracy map. In some aspects, the processor 210 of computer 102a is configured to generate the accuracy map. In some aspects, the processor 210 is configured to retrieve the accuracy map from the memory 220, the network interface card 260, or the input device 230. Further details regarding determining the accuracy of the 3-D model of the physical object and accuracy maps will be discussed below with reference to FIG. 5.

At block 406, the process proceeds by generating a simulated representation of a device. In some aspects, the device may include a surgical device, such as a surgical guide, an orthotic device, a prosthetic device, or a surgical tool. For example, a surgical guide or other medical or surgical device, tool, etc. may be designed and a model of the device may be generated to represent the designed device. At block 408, the process determines whether the simulated representation of the device satisfies a stability threshold. The stability threshold may be set to determine whether the simulated representation of the device is sufficiently stable for the particular application for which the device is to be used. For example, the stability threshold may be used to determine whether a simulated surgical guide design is stable with respect to the contact surface of a body part for which the guide is to be used. In some aspects, it is determined whether the simulated representation of the device satisfies the stability threshold based on a stability score. In some aspects, the processor 210 is configured to generate the stability score. In some aspects, the processor 210 is configured to retrieve the stability score from the memory 220, the network interface card 260, or the input device 230. The process may continue by generating a second simulated representation of the device if the simulated representation of the device does not satisfy the stability threshold. The process may then determine whether the second simulated representation satisfies the stability threshold. The process may continue to generate subsequent simulated representations of the device until one of the representations satisfies the stability threshold. For example, various device designs may be analyzed with respect to the stability of the device on the contact surface of a physical object upon which the device will be used. Further details regarding determining whether the simulated representation of the device satisfies a stability threshold will be discussed below with reference to FIG. 5.

At block 410, the process continues by simulating a fit of the device on the 3-D model of the physical object if the simulated representation of the device satisfies the stability threshold. In some aspects, simulating a fit of the device on the 3-D model includes simulating a fit of the device on one or more variations of the 3-D model. Simulating a fit of the device on the 3-D model may further include registering the simulated representation of the device on top of the physical object to determine a best fit. For example, the best fit may be determined when a number of data points on the simulated representation of the device match with a corresponding set of data points on the 3-D model of the physical object. In some aspects, simulating a fit of the device on the 3-D model may include simulating a fit of a surgical device (e.g., a surgical guide, surgical tool, orthotic, or a prosthetic) on one or more variations of the 3-D model of a human body part. The output of the fit simulation may include a resulting position of the device on the object. At block 412, the process determines whether the simulated fit of the device on the 3-D model of the physical object is within a tolerance threshold. In some aspects, the resulting position of the device on the object may be compared to the tolerance threshold to determine whether the device will be used during its planned application within a bounded region of a planned position for which the device was designed with respect to the object. Further details regarding simulating a fit of the device on the 3-D model of the physical object and determining whether the simulated fit is within a tolerance threshold will be discussed below with reference to FIG. 5.

At block 414, the method generates an approved design of the device if the simulated fit is within the tolerance threshold. If the simulated fit is not within the tolerance threshold, the process may proceed to reject the design case regarding design of the device. In some aspects, a printer (e.g., output device 240) is configured to generate the device based on the approved design of the device.

Figure 5:
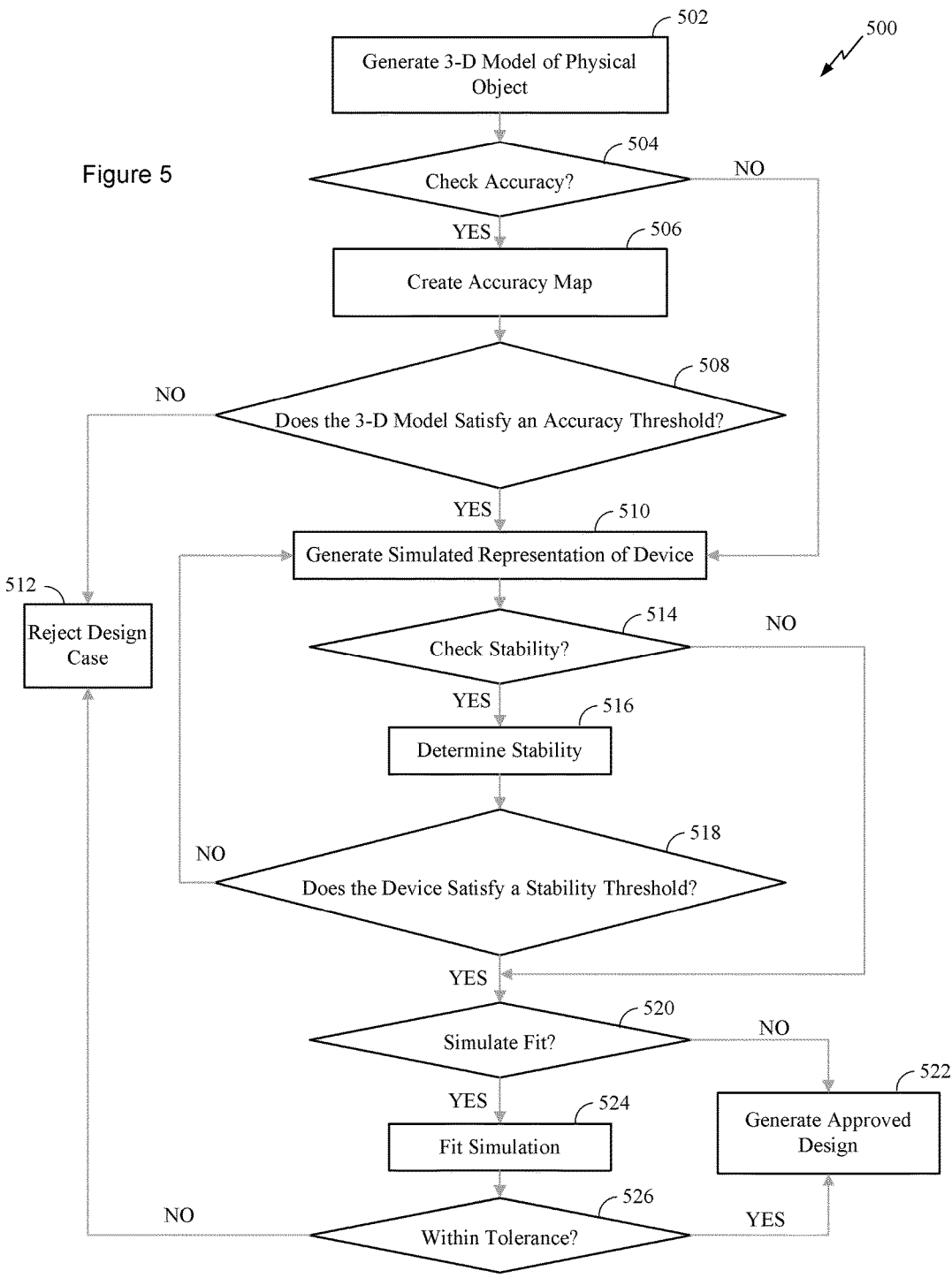
FIG. 5 illustrates another process for designing and generating a device using accuracy and stability analysis.

FIG. 5 illustrates another example of a process for designing a device. In some aspects, the process 500 may be implemented by various means, such as computer 102*a* using, for example, processor 210. At block 502, the process begins by generating a 3-D model or digital representation of a physical object. In some aspects, the physical object may include, for example, a human body part, such as a bone (e.g., femur, humerus, spine, etc.), a leg, an arm, an ankle, etc.

In some aspects, as described in further detail below, a simulated model may be used in a fitting method to implement 2-D image based segmentation of the physical object to create a 3-D model of the object. For example, the simulated model relating to the physical object may be compared with images of the object in order to generate the 3-D model. For example, the simulated model may include a statistical shape model representing the physical object that may be compared with or fit to one or more images (e.g., X-ray or other medical scan) of the physical object. In some aspects, multiple images from different angles may be used in the fitting to provide multiple cases for fitting the simulated model. In some aspects, the images may include at least a view from the coronal and sagittal plane of physical object. The statistical shape model may be a 2-D or 3-D model representing the physical object and may correspond to a theoretical expected object with similar characteristics as those of the physical object. In some aspects, an iterative closest point process, or a variant thereof, may be used in generating the 3-D model of the physical object. For example, the comparison or fit of the statistical shape model to the one or more images may be done by registering or aligning the statistical shape model with the image. The registration may be done by selecting points on the statistical shape model and/or the image and then matching the various data points on the statistical shape model with data points on the image. Points may be selected from the statistical shape model only, the image only, or from both the statistical shape model and the image. Various matching methods may be used. For example, matching may be done by determining the nearest points on the image relative to given points on the statistical shape model. Further, various translations and rotations of the statistical shape model may be tested relative to the image in order to match corresponding points and align the statistical shape model and the image shape. The process may iteratively select and match points on the statistical shape model and the image in order to refine the 3-D model and minimize the distance between corresponding points on the statistical shape model and the image shape. The result of the registration tailors the statistical shape model to the image in order to accurately generate a 3-D model of the physical object. One example may include generating a 3-D model of a patient's femur. In this example, an X-ray image of a patient's femur may be obtained. Further, a statistical shape model including anatomical knowledge of a femur for a theoretical person with similar characteristics as those of the patient (e.g., sex, age, height, weight, etc.) may be registered or aligned with the X-ray image in order to generate a 3-D model of the patient's femur. Various data points on the statistical shape model and/or the X-ray image may be selected. The data points from the statistical shape model may then be matched with data points on the X-ray image. After the matching is complete, a 3-D model of the patient's femur is generated. Further details regarding generation of a 3-D model from 2-D images by performing 2-D image based segmentation using a simulated model will be discussed below.

In some aspects, the 3-D model of the physical object may be generated based on 3-D imaging techniques, such as segmentation of 3-D image data to create the 3-D model. For example, various different 3-D images of the physical object may be obtained (e.g., magnetic resonance imaging (MRI) or computed tomography (CT) imaging) and segmented in order to create the 3-D model. In some aspects, the 3-D model may be based on a 3-D reconstruction of CT or MRI images.

In some aspects, as described above, a simulated model may be used to implement 2-D image based segmentation of a physical object to create a 3-D model of the object. The 2-D based segmentation is a statistical method of building up a 3-D model of the physical object from one or more 2-D images like X-rays. In some aspects related to medical applications, one or more X-ray images alone may not include sufficient information to build up a reliable 3-D model of a physical object depicted in the X-ray (e.g., a bone). Accordingly, in order to do build up a reliable 3-D model, a simulated model including anatomical knowledge relating to the object in the X-ray may be used to interpret the X-ray. For example, the anatomical knowledge may be condensed in a statistical shape model (SSM). The SSM may be used in a fitting method to implement the 2-D image based segmentation of the physical object to create the 3-D model by fitting the SSM to the 2-D image. In order to design a 3-D model that is accepted by industry participants (e.g., medical companies, surgeons, etc.), information relating to the accuracy of the resulting geometry of the model may be provided. Accordingly, the final result of the fit includes a 3-D model including a fitted geometry (e.g., a Standard Tessellation Language (STL) model) and also an accuracy map. Techniques for assessing and indicating the accuracy and quality of the 3-D model using accuracy maps are discussed below at blocks 504 and 506.

As noted above, the anatomical knowledge of the physical object may be condensed in a SSM. The SSM may be used to understand what is in a set of X-rays. The SSM also has a strong statistical aspect and may be used in the fitting method and the related accuracy map. Principal component analysis (PCA) may be used to generate the SSM. The input of a PCA analysis includes a training set. Each shape of the physical object represented by the SSM may be transformed into a vector and each vector may be transformed back to the corresponding shape. Accordingly, each shape may be considered to be a corresponding vector, and each vector may be considered to be a corresponding shape. The training set is thus a set of vectors. When doing the PCA, it may be implicitly assumed that the vectors are part of a population that has a Gaussian distribution and that the training set is a representative subset. The result of the PCA provides the SSM and includes an average shape (or corresponding vector), a set of principal components, and a standard deviation for each principal component.

The probability distribution function of the training set is used in determining the various principle components. The distribution function $f$ of the training set is:

$$f(\vec{x}) = \frac{1}{(2\pi)^{\frac{n}{2}}|\Sigma|^{\frac{1}{2}}} e^{-\frac{1}{2}(\vec{x}-\vec{\mu})^T \Sigma^{-1}(\vec{x}-\vec{\mu})}$$

Where $\Sigma$ is the covariance matrix, is the number of cases in the training set, x is the stochastic variable, and $\mu$ is the mean vector.

Principal component analysis (PCA) is used to determine the direction (around the average $\mu$) that has the highest standard deviation ($\sigma$), which indicates where the population varies the most and may be referred to as maximal standard deviation $\sigma_1$ and direction $\vec{v}_1$. The direction $\vec{v}_1$ is the first principal component. Taking into account the subspace of the population of all statistically, stochastically independent vectors of the principal direction (the remainder of the population), a maximal standard deviation $\sigma_2$ and corresponding direction $\vec{v}_2$ may be determined. The direction $\vec{v}_2$ is the second principal component. The same technique may be used to determine the remaining principle components $\vec{v}_3 \ldots \vec{v}_n$. The result is a set of principal components, each statistically independent from the other principle components. The principal components may be ordered from important (e.g., having a large standard deviation) to insignificant (e.g., having nearly zero standard deviation).

Once the principal components are determined, a covariance matrix $\Sigma$ of a data matrix M (centralized around the average) is determined. The data matrix M is a matrix with rows including the individual data vectors of the training set. The covariance matrix $\Sigma$ of M is determined using:

$$\Sigma = \frac{1}{n} M^T M$$

Where $\Sigma$ is the covariance matrix, M is the data matrix, is the number of elements in the training set, and $M^T$ is the transpose of M.

The covariance matrix $\Sigma$ of M may be used in the generation of the resulting SSM. The principal components are then the eigenvectors of $\Sigma$ and the eigen values $\lambda_i$ are times the variances $v_i$ (with $v_i = \sigma_i^2$). The vectors themselves are orthonormal. A singular value decomposition (SVD) technique may be implemented on the data matrix M in determining the resulting SSM using:

$$M = U \cdot S \cdot V^T$$

Where U are the left singular vectors, S is a diagonal matrix containing the singular values, V are the right singular vectors, and $V^T$ is the transpose of V. The SVD of the data matrix may be included in the covariance matrix $\Sigma$ equation to generate the SSM:

$$\Sigma = \frac{1}{n} M^T M$$
$$= \frac{1}{n}(U \cdot S \cdot V^T)^T \cdot (U \cdot S \cdot V^T)$$
$$= \frac{1}{n} V \cdot S \cdot U^T \cdot U \cdot S \cdot V^T$$
$$= \frac{1}{n} V \cdot S^2 \cdot V^T$$

As a result, the SSM is generated for use in the fitting method. The SSM includes the mean vector $\mu$, an optional scale, a set of principle components, and a standard deviation for each principle component. The principal components make up the columns of the matrix V. The matrix containing the principal components may also be called P (P=V). The training set used in generating the SSM may include a set of actual cases related to the particular object being modeled and each shape vector of the object may have a particular dimensional space. Each of the cases corresponds to one vector and thus one row of the data matrix M. For example, a set of 15,000 cases may be available to choose from for a bone (e.g., a femur) and each shape vector for the bone may have a dimensional space of 117360 mm. One of skill in the art will understand that the dimensional space may also be measured in inches or in any other unit. The resulting data matrix M has dimensions of 15000×

117360, which corresponds to a large amount of data (e.g., 13 GB). A sample size of the data matrix M may be determined in order to reduce the amount of data by taking into account various factors, including an intrinsic dimension and errors or noise.

The intrinsic dimension is the dimension of a subspace of the dimensional space. Further, the training set includes measured data and will thus contain measuring errors or noise. The measuring errors are not relevant in determining the SSM because they do not represent geometrical components of the SSM and may be filtered out. Filtering of the measuring error may be done by assuming that the measuring error is not systematic and is small relative to the dimensions of the true geometry, resulting in the error being present in the principal components that have a small standard deviation. Accordingly, the measuring error may be filtered out by not taking into account the smallest principal components.

In order to determine the intrinsic dimension of the dataset and filter the noise to determine the training set size, a small, random sub-sample of the total available set of cases may be selected. For example, 200 cases may be selected and a PCA may be conducted on the sub-sample of cases. An average vector and 199 principal components with 199 corresponding standard deviations may be determined. This may be repeated by increasing the sub-sample size by 10% each time. During the PCA analysis, the principal components and their standard deviations may be analyzed to determine when the large components with corresponding standard deviations converge and become stable. At the point when a specific component no longer changes as new cases are added to the PCA, it is determined that the sample size is large enough for that component. Further, as the process continues, the number of cases in the PCA and the number of stable principal components increases. However, once a particular sample size is reached, there will be very few additional stable principal components. The analysis is stopped at the point that this particular sample size is reached. The stable principal components are used and the number of stable components is a pragmatic version of the intrinsic dimension. The remaining principal components are considered to be noise and may be disregarded. As a result, an appropriate sample size of the data matrix M is determined for the particular application and a SSM may be generated based on the sample size of the data matrix M.

As described above, the SSM may be used in the fitting method and with regard to the related accuracy map. A SSM may be considered to be a family of shapes. By feeding the SSM a shape combination vector $\vec{k}$, a single shape $\vec{m}$ may be determined using:

$$\vec{m}(\vec{k}) = \vec{m}_{av} + P \cdot \vec{k}$$

Where $\vec{k}$ is a shape combination vector, $\vec{m}$ is a single shape vector, P is the matrix containing the principal components, and $\vec{m}_{av}$ is an average vector. Each coordinate in the shape combination $\vec{k}$ is normally distributed with a standard deviation and all coordinates are stochastically independent. As a result, the covariance matrix $\Sigma$ in the Gaussian distribution may reduce to a diagonal matrix which may be represented by its diagonal vector $\vec{\sigma}$. The principal components are the directions that are statistically independent, which is reflected by the fact that the resulting covariance matrix of the transformed data is diagonal.

Figure 6:
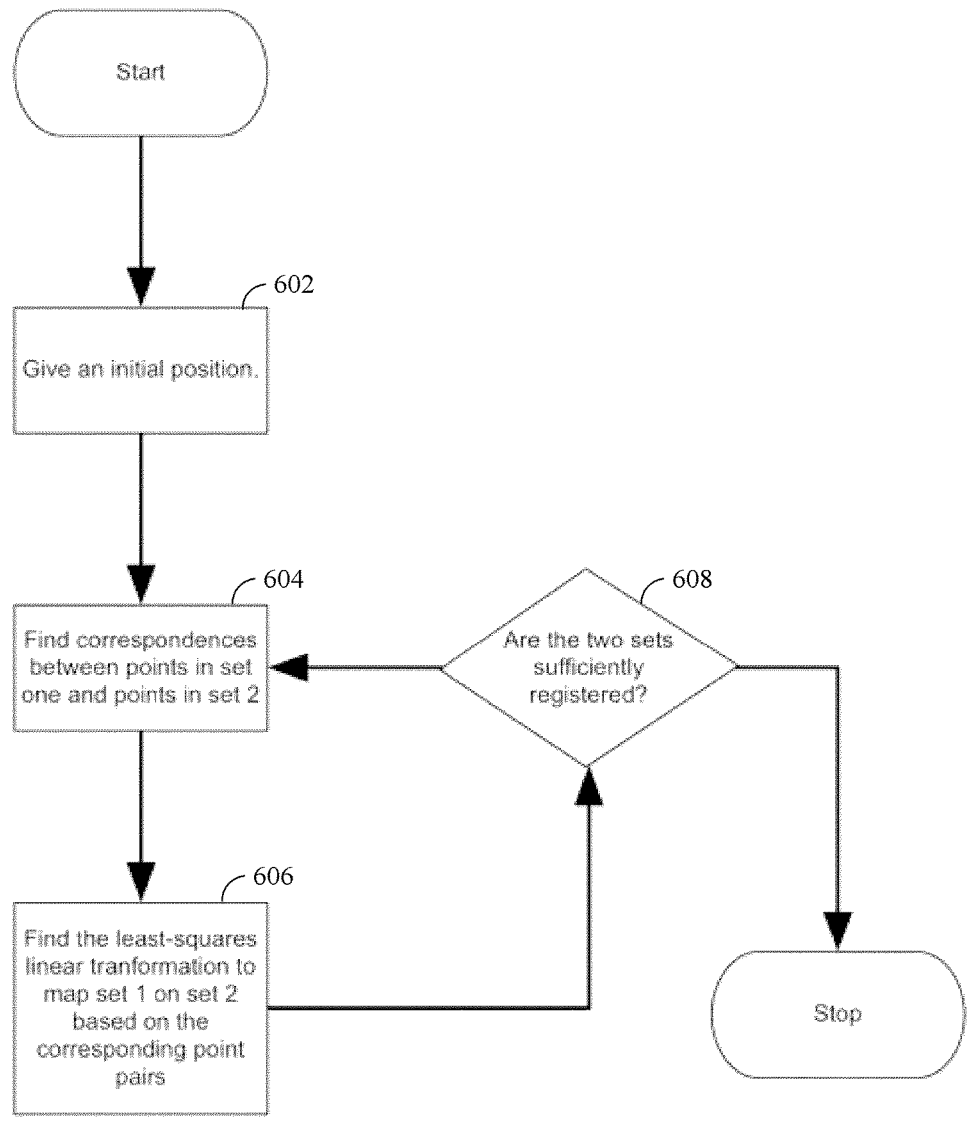
FIG. 6 illustrates a process of registering a 3-D surface model to a point cloud.

As noted above, a fitting method may be used in generating the 3-D model of the physical object using the SSM. The fitting method may include a variation of an iterative closest point (ICP) technique. The ICP technique is a method to register a 3-D surface model to a point cloud using an n-points registration that includes mapping a list of points to a corresponding list of points by identifying a least-squares orthonormal transformation and scale used to map the corresponding points onto each other (see below). Given one list of points $\vec{a}_i$ and a corresponding list of target points $\vec{b}^i$, the orthonormal transformation (translation $\vec{t}$ and rotation R) and scale s that minimizes the function includes:

$$F(\vec{t}, R, s) = \sum_{i=1}^{n} d(s \cdot R \cdot \vec{a}_i + \vec{t}, b_i)^2$$

Where s is the optional scale, $\vec{t}$ is the translation vector, R is the rotation matrix, $\vec{a}_i$ is the list of points, and $\vec{b}_i$ is the list of target points. The s, R, and $\vec{t}$ may then be applied to the SSM. The ICP technique applies the n-points registration iteratively as shown in FIG. 6. As illustrated in FIG. 6, the ICP technique registers a point cloud to a surface (or another point set) or vice versa. At block 602, an initial position is given for the SSM. An initial scale and shape of the SSM may also be given at block 602. At block 604, correspondences between points in a first set and points in a second set are found. At block 606, the least-squares linear transformation is found to map the first set of points to the second set based on the corresponding point pairs. At block 608, it is determined whether the two sets are sufficiently registered. If so, the process comes to an end. If the two sets are not sufficiently registered, the process proceeds to block 604. As a result, the registration is performed by calculating the closest points (finding correspondences between the two sets) and registering them using the n-points registration. The process is iterated it until the two sets are sufficiently registered.

As noted above, a SSM may be fit to identified points on an object using a variation of the ICP technique, using a transformation as a parameter. The input may include a set of target points and, for each target point, a corresponding point on the SSM that is desired to go to the target point.

The least-squares fitting of an SSM includes fitting of a linear system within the SSM. Each shape within the SSM may be represented by a combination vector $\vec{k}$:

$$\vec{m}(\vec{k}) = \vec{m}_{av} + P \cdot \vec{k}$$

Where $\vec{k}$ is a combination vector, $\vec{m}$ is a shape vector, $\vec{m}_{av}$ is an average vector, and P is the matrix containing the principal components. A least squares solution $\vec{k}_{ls}$ may be determined and used in the $\vec{m}(\vec{k})$ equation above to calculate the least squares shape vector $\vec{m}_{ls}$.

In some aspects, the vector $\vec{m}$ may only be partially known, which means that only some of its coefficients are known. The known and unknown coefficients may be represented by a shape vector filter including a binary vector of the same size as the shape vector. Each true value of the binary vector may indicate that the target position of the individual coordinate is known and each false value may indicate that that the individual coordinate is not known. The target coordinates are then stored in a vector $\vec{m}_r$ of a smaller dimension than $\vec{m}$ that is equal to the number of true values in the shape vector filter. A matrix Q may be created that includes the rows of P for which the shape vector filter has true value. The vector $\vec{k}$ may then be determined such that:

$$\vec{m}_r = \vec{m}_{avr} + Q \cdot \vec{k}$$

Where $\vec{k}$ is a combination vector, $\vec{m}_r$ is a reduced shape vector, $\vec{m}_{avr}$ is a reduced average vector, and Q is the matrix including the rows of P for which the shape vector filter has a true value. A reduced least squares shape vector $\vec{m}_{rls}$ may be determined by solving the $\vec{m}_r$ equation above using a singular value decomposition (SVD) technique on the matrix Q:

$$Q = U \cdot S \cdot V^\tau$$

Where Q is the matrix including the rows of P for which the shape vector filter has a true value, U are the left singular vectors, S is a diagonal matrix containing the singular values, V are the right singular vectors, and $V^\tau$ is the transpose of V. The decomposition using SVD allows aspects of Q to be analyzed. The diagonal matrix S contains the singular values of Q. If all singular values are different from 0, S may be inverted:

$$S = \begin{pmatrix} s_1 & \cdots & 0 \\ \vdots & \ddots & \vdots \\ 0 & \cdots & s_n \end{pmatrix} \Rightarrow S^{-1} = \begin{pmatrix} s_1^{-1} & \cdots & 0 \\ \vdots & \ddots & \vdots \\ 0 & \cdots & s_n^{-1} \end{pmatrix}$$

The solution to the $\vec{m}_r$ equation is then:

$$V \cdot S^{-1} \cdot U^\tau = \vec{k}$$

In the event there are $s_i$ singular values numerically close to 0, a 0 may be used instead of using $s_i^{-1}$, which results in a matrix $S^+$. The solution resulting from the $\vec{m}_r$ equation above is then:

$$V \cdot S^+ \cdot U^\tau \cdot (\vec{m}_r - \vec{m}_{avr}) = \vec{k}_{ls}$$

The least squares solution $\vec{k}_{ls}$ may further minimize using:

$$\|\vec{m}_r - \vec{m}_{avr} + Q \cdot \vec{k}\|$$

The result of the SVD on the matrix Q may be used to determine an optimal or best solution vector $\vec{k}_{op}$ with the highest probability for fitting the SSM, instead of using a least squares solution $\vec{k}_{ls}$. Looking at the $\vec{k}_{ls}$ equation above, the columns of V that have a zero as a corresponding inverted singular value may be included in a matrix V'. Adding a linear combination of the inverted singular values of zero to the least squares solution has no effect on the resulting fitting residue. Fitting residue includes the difference between an observed value and the fitted value provided by the model. Rather than taking the least squares solution $\vec{k}c_{ls}$, any other solution may be taken from the space defined by $\vec{k}_{ls}$ and spanned by V'. Accordingly, $\vec{k}$ may be determined by:

$$\vec{k} = \vec{k}_{ls} + V' \cdot \vec{t}$$

Where $\vec{k}_{ls}$ is the least squares solution, $\vec{t}$ is a vector of length k, the length k is the number of zeros on the diagonal of $S^+$, and V' is a matrix including the columns of the matrix V that have a zero as an inverted singular value. Any $\vec{t}$ may be chosen because each value has the same fitting residue. As noted above, each coefficient of the SSM that is being determined is normally distributed with a known standard deviation. Accordingly, the distribution function of $\vec{k}$ is:

$$f(\vec{k}) = \frac{1}{(2\pi)^{\frac{n}{2}} |\Sigma|^{\frac{1}{2}}} \exp\left(-\frac{1}{2} \vec{k}^\tau \cdot \Sigma^{-1} \cdot \vec{k}\right)$$

As described above, the principal components are statistically independent. As a result, the covariance matrix $\Sigma$ is diagonal:

$$\Sigma^{-1} = \begin{pmatrix} \frac{1}{\sigma_1^2} & \cdots & 0 \\ \vdots & \ddots & \vdots \\ 0 & \cdots & \frac{1}{\sigma_n^2} \end{pmatrix}$$

The distribution function g of all of the best or optimal solutions with the highest probability is:

$$g(\vec{t}) = \frac{1}{(2\pi)^{\frac{n}{2}} |\Sigma|^{\frac{1}{2}}} \exp\left(-\frac{1}{2} (\vec{k}_{ls} + V' \cdot \vec{t})^\tau \cdot \Sigma^{-1} \cdot (\vec{k}_{ls} + V' \cdot \vec{t})\right)$$

In order to determine the optimal fitting solution with the highest probability, $\vec{t}_{op}$ may be determined where g reaches its maximum. In order to maximize what is in the exponent of the $g(\vec{t})$ equation above, the $-\frac{1}{2}$ may be disregarded and the portion F that is in the exponential function is minimized using:

$$F(\vec{t}) = (\vec{k}_{ls} + V' \cdot \vec{t}) \cdot \Sigma^{-1} \cdot (\vec{k}_{ls} + V' \cdot \vec{t} \times)$$

The maximum (gradient) of F may then be found using:

$$\nabla F(\vec{t}_{op}) = \vec{0}$$
$$\Rightarrow 2(\vec{k}_{ls} + V' \cdot \vec{t}_{op})' \cdot \Sigma^{-1} \cdot V' = \vec{0}$$
$$\Rightarrow \vec{t}_{op} \cdot V'^\tau \cdot \Sigma^{-1} \cdot V' = -\vec{k}_{ls}^\tau \cdot \Sigma^{-1} \cdot V'$$
$$\Rightarrow \vec{t}_{op} = -\vec{k}_{ls}^\tau \cdot \Sigma^{-1} \cdot V' \cdot (V'^\tau \cdot \Sigma^{-1} \cdot V')^{-1}$$
$$\Rightarrow \vec{t}_{op} = -\vec{k}_{ls}^\tau \cdot \Sigma^{-1} \cdot V' \cdot \Sigma'$$

Where $\Sigma' = (V'^\tau \cdot \Sigma^{-1} \cdot V')^{-1}$, which is a shorthand notation that will be used further below with regard to accuracy maps. Accordingly, the optimal or best solution $\vec{k}_{op}$ becomes:

$$\vec{k}_{op} = \vec{k}_{ls} + V' \cdot \vec{t}_{op}$$

As a result, instead of determining the least squares solution $\vec{k}_{ls}$, the statistically most likely solution $\vec{k}_{op}$ in a subspace of all best solutions is determined. At this point, the probability function above (η) reaches a maximum and thus the probability is at its highest. This technique may be referred to as a high probability optimal fitting technique and may be used in a shape fitting to fit the scale and shape parameters of the SSM to a set of points on an object and/or to create one or more accuracy maps.

Figure 7:
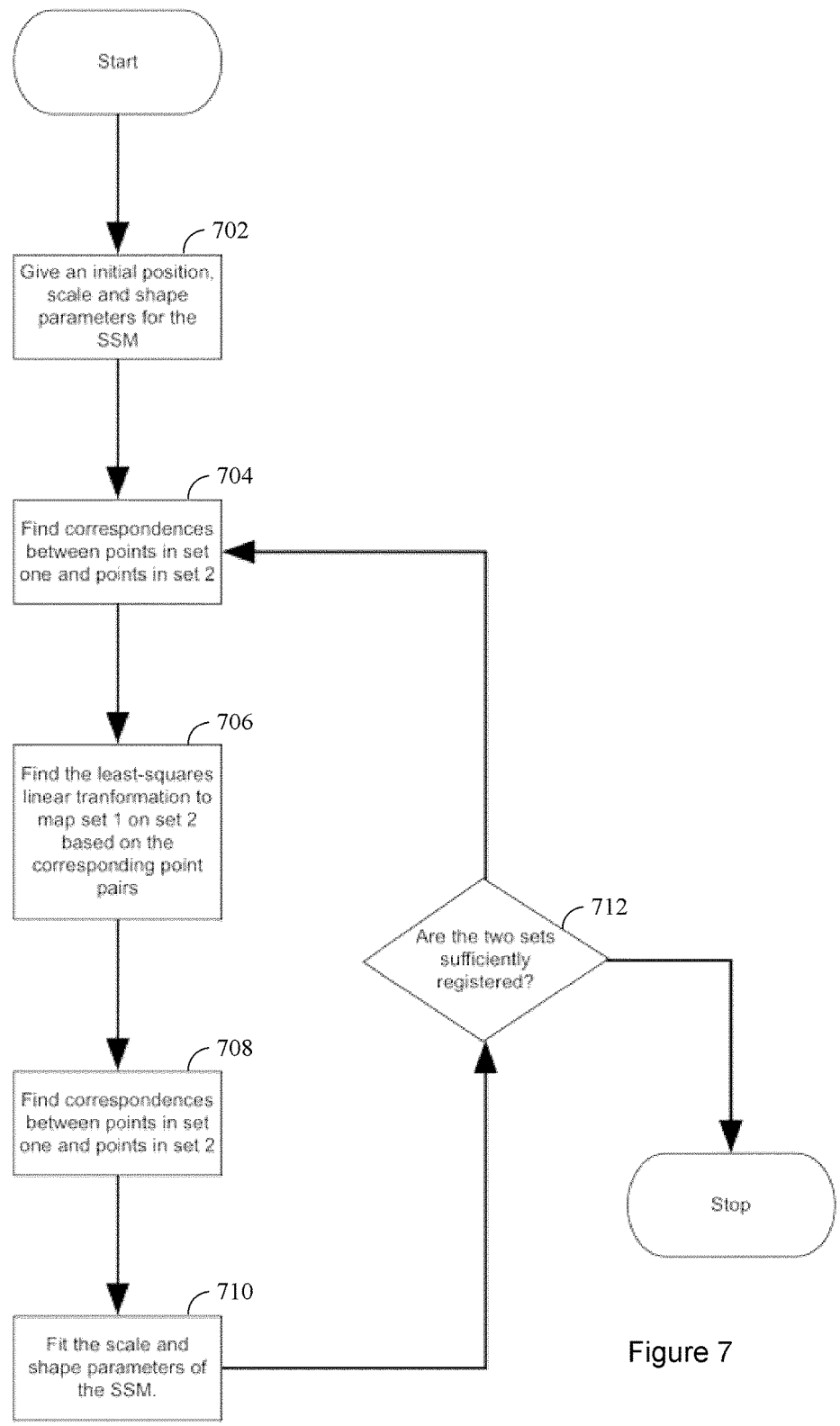
FIG. 7 illustrates a process of fitting a statistical shape model (SSM) to a point cloud.

Prior to explaining how to fit a SSM to an X-ray, how to register and fit a SSM to a 3-D point cloud will be explained according to FIG. 7. At block 702, an initial position of the SSM is given along with scale and shape parameters for the SSM. At block 704, correspondences between points in a first set and points in a second set are found. In some aspects, the first set includes the SSM and the second set includes the 3-D point cloud. The original ICP technique (not the variation thereof) described above may be used to identify the corresponding point pairs between the 3-D point cloud and the points in the SSM. At block 706, a position fit is done by finding the least-squares linear transformation to map the first set of points to the second set based on the corresponding point pairs. At block 708, correspondences are found between points in the first set and the second set. At block 710, a shape fitting is done by fitting the scale and shape parameters of the SSM to the second set of points. The high probability optimal fitting technique described above may be used to do the shape fitting. At block 712, it is determined whether the two sets are sufficiently registered. If so, the process comes to an end. If the two sets are not sufficiently registered, the process proceeds to block 704 and continues the process.

Figure 8:
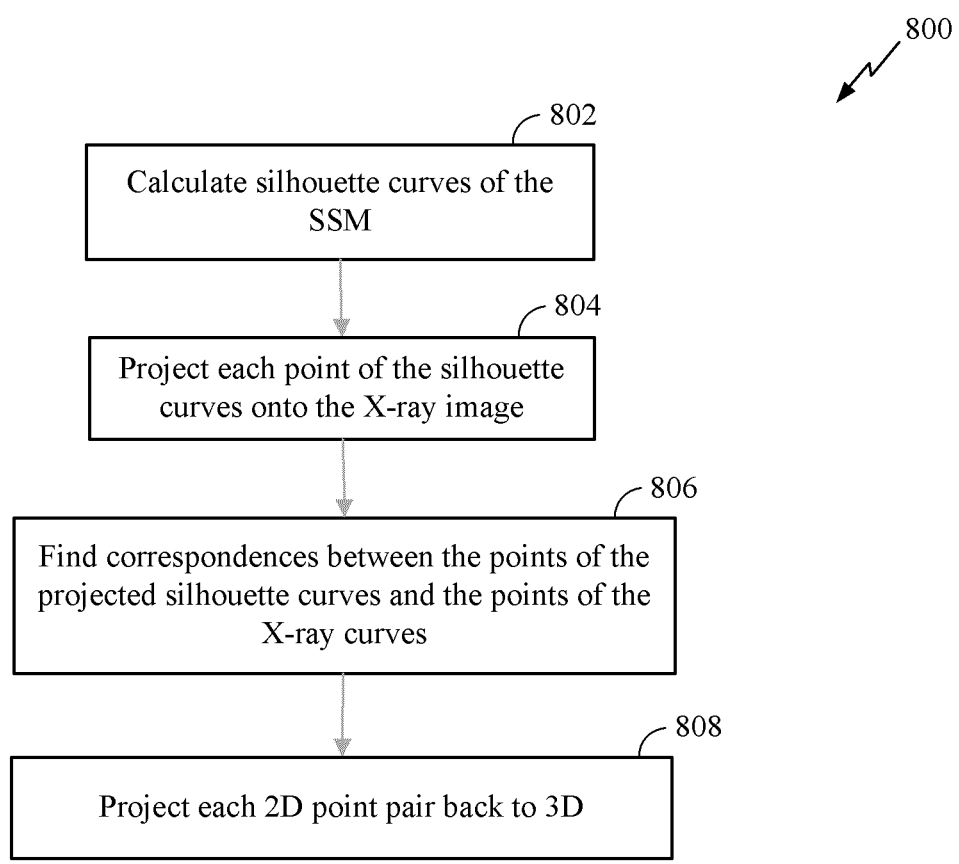
FIG. 8 illustrates a process of obtaining 3-D points from 2-D points of an X-ray.
Figure 9:
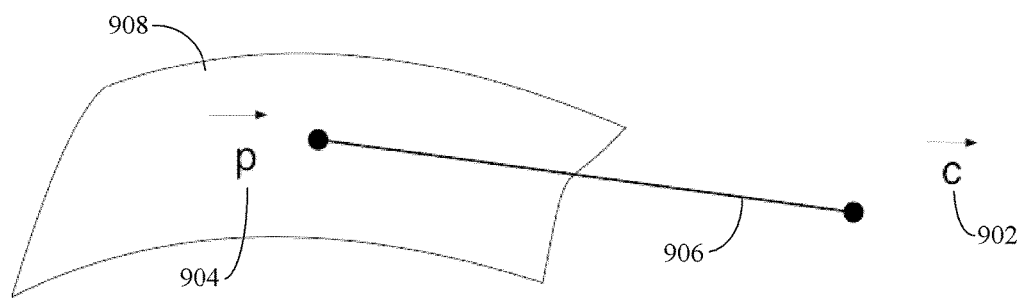
FIG. 9 illustrates an example of a silhouette point or curve of a model.

In order to fit a SSM to one or more X-rays, which include only 2-D points, 3-D points must be built from the 2-D X-ray images during the fitting method. A back projection method may be used to obtain 3-D points from the one or more X-rays, which may provide the corresponding point pairs for use in the fitting method. An exemplary back projection method 800 is illustrated in FIG. 8, and will be discussed below. In order to fit the SSM to the X-ray, corresponding point sets in 3-D must be found between the SSM and the X-ray. One set comes from the SSM and the other set is related to the contour points or lines on the X-ray, which are 2-D. In some aspects, the contour points or lines of the X-ray may be determined based on the areas of the images that provide the highest degree of accuracy. In some aspects, the contour points or lines on the X-ray may be generated using various tools, including manual edge detection or automatic tools such as a Canny edge detection algorithm, a Sobel edge detection algorithm, etc. Beginning with the set of points on the SSM, points or curves may be determined on the SSM that correspond to the contour points or lines on the X-ray. These points or curves may include silhouette points or curves. FIG. 9 illustrates an example of a silhouette point or curve. A silhouette point or curve is a curve or point 904 on the SSM 908 where the connecting line 906 between the SSM point 904 and a source point 902 is tangent to the SSM 908. The source point 902 includes a source point of an imaging apparatus relative to the object being captured and may be obtained by determining the position(s) of the imaging apparatus. In some aspects, the position of the source point may be obtained or determined at the moment of taking the images so that the position of the imaging apparatus (source point) relative to a detector plate or relative to the object is determined and stored for further use. In some aspects, the position of the source point may be measured based on tools included in the images themselves. These tools may allow the position of the imaging apparatus to be determined on the basis of the image. For example, these tools may include an imaging calibration device (e.g., a radiographic calibration device), such as those described in PCT/EP2012/058242 (which is incorporated herein by reference in its entirety). These calibration devices make it possible to obtain an improved geometrical accuracy and grey-value accuracy of the one or more X-rays.

Returning to FIG. 8, the method 800 includes calculating the silhouette curves or points of the SSM at block 802. In order to find the silhouette points or curves on the SSM, a real-valued function g on all points $\vec{p}$ of the SSM may be defined as follows:

$$g(\vec{p}) = n(\vec{p}) \cdot (\vec{p} - \vec{c})$$

Where $\vec{p}$ is the SSM point (e.g., point 904), $\vec{c}$ is the source point (e.g., point 902), and is the normal to the SSM in the point $\vec{p}$. The value of this function g is zero for the points of the SSM on the silhouette curves. Therefore, the zero-curves of this real-valued function are found by looking to each triangle and checking the corresponding configuration. To do this, each point having a function g value above a threshold (e.g., zero) and each point having a function g value below the threshold is determined. FIG. 10 illustrates one example with eight (2^3) possible cases for each triangle. During the calculation of the silhouette curves, each triangle is classified as one of these cases and the line pieces within each triangle all together are the silhouette curves. This method for determining silhouette curves or points may be referred to as a marching triangles approach, and relates to a marching cubes technique.

The silhouette curves may then be projected on the X-ray. For example, at block 804, the method 800 projects each point of the silhouette curves onto the X-ray image. At block 806, the method continues by finding correspondences between the points of the projected silhouette curves and the points of the X-ray curves. The correspondence may include point pairs that are mutually the closest. At block 808, the method continues by projecting each 2-D point pair back to 3-D. In each point pair, there is one point that is a projected silhouette point and one point that is an X-ray contour point. Back projecting the projected silhouette point includes using the original 3-D silhouette point. Back projecting the X-ray contour point includes using the closest point to the 3-D silhouette point on the line connecting the contour point and the source position. As a result, a set of corresponding point pairs is obtained. Once the 3-D points have been built up using back projection, the SSM may be fit to the X-ray.

Figure 11:
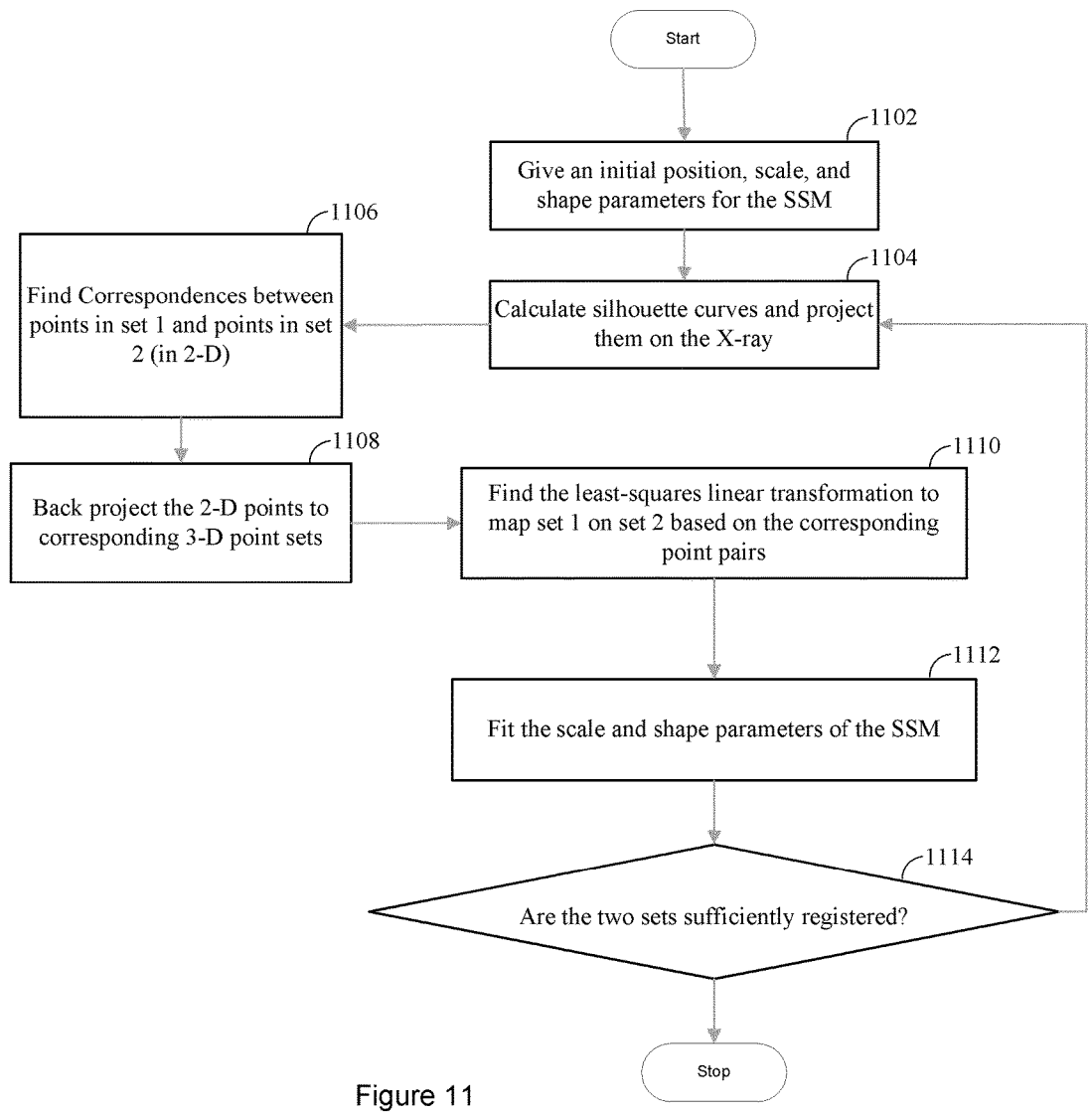
FIG. 11 illustrates a process for fitting a SSM to one or more X-rays.

FIG. 11 illustrates an exemplary process for fitting a SSM to one or more X-rays. At block 1102, initial position, scale, and shape parameters for the SSM are given. At block 1104, the silhouette points or curves on the SSM are calculated and projected on the X-ray. At block 1106, correspondences between points in a first set (set 1) and points in a second set (set 2) are found. The first set includes points on the SSM and the second set includes 2-D points on the X-ray. At block 1108, the 2-D point sets of the X-ray are back projected to corresponding 3-D point sets. As a result, each 2-D point pair is projected back to 3-D. In some aspects, steps 1104-1108 may be repeated in order to increase the stability and speed of the fitting method. At block 1110, a position fit is done by finding the least-squares linear transformation and using the transformation to map the first set of points on the SSM to the second set of back projected 3-D points of the X-ray based on the corresponding point pairs. At block 1112, a shape fitting is done by fitting the scale and shape parameters of the SSM to the back projected 3-D points of the X-ray. The high probability optimal fitting technique described above may be used to do the shape fitting. At block 1114, it is determined whether the two sets of points are sufficiently registered. If so, the process comes to an end. If the two sets of points are not sufficiently registered, the process proceeds to block 1104 and continues the process.

Accordingly, the fitting method allows the SSM to be fit to X-ray images in order to create a 3-D model of the physical object depicted in the X-rays. As described above, the accuracy or reliability of the 3-D model of the physical object is important in order to effectively design a device based on the 3-D model and for possible use with the physical object. In order for the 3-D model to be accepted by industry participants, information relating to the accuracy of the resulting geometry of the model may be provided. Accordingly, the fitting method described above may further include one or more accuracy maps in addition to the fitted geometry described above. Returning to FIG. 5, the process 500 continues at block 504 by determining whether to check the accuracy of the 3-D model of the physical object. The process continues to block 510 to generate a simulated representation of a device if the process determines not to check the accuracy of the 3-D model. If the process determines to check the accuracy, an accuracy map is created at block 506. The determination of whether to check the accuracy of the 3-D model may be based on a user input, on the specific application related to the device design, or any other design constraint related to the physical object and/or the device design. Different types of accuracy maps may be created to indicate different types of uncertainty, accuracy, inaccuracy, or error at each point of the 3-D model, and may be combined to create a single accuracy map, as described in further detail below. The surface of the 3-D model may be divided into useable and unreliable zones to create the accuracy maps. The zones being may be divided based on the particular application of the device.

An accuracy map provides a complete image on how accurate the result is in each point of the 3-D model and may indicate the confidence of each point of the fitted surface. In some aspects, standard deviation ($\sigma$) may be used to model the accuracy and the accuracy map may include a mask indicating the standard deviation at each point. An assumption may be made that all parameters are normally distributed.

As described above, a SVD decomposition on the matrix Q may be done, and, instead of finding a least squares solution, an optimal or best solution vector $\vec{k}_{op}$ may be determined with a high probability for fitting the SSM by using a high probability optimal fitting technique. A least-squares fit may become unstable with highly detailed SSMs that include small but meaningful components. In some aspects, the high probability optimal fitting technique may instead be used with highly detailed SSMs. The high probability optimal solution fitting technique may be used in the generation of the resulting 3-D model and the accuracy maps. For example, as described above, the high probability optimal solution approach may be used to define a new quality measure by optimizing a target function in order to obtain a high probability best fit. Regarding the generation of accuracy maps, the high probability optimal fitting approach may be used to provide a detailed model of how accurate and reliable the resulting 3-D surface model is at each point of our model. This reliability is represented by an accuracy map: it gives a range (or confidence interval) for each point of the model. Further, the accuracy maps may be used to further optimize the fitting using a range threshold. There are several sources of error (described below) that increase the range within the model, hence there are several accuracy maps. All of these accuracy maps may be combined into one total accuracy map. The range threshold may be determined and used to minimize the range of the total accuracy map. Adjusting the range threshold may change the range of each type of error described below in a total accuracy map. For example, increasing the range threshold may increase the range in the insufficient input error described below, and may reduce the range in the propagated input error discussed below. As noted above, the accuracy maps contain a certainty interval at each point of the resulting 3-D model, and thus the total accuracy map provides a measure for the quality of the fit at each point. The range threshold may be set in such a way that the combined map has the smallest ranges. The range threshold may be set so that different quality measures may be defined for different applications. For example, one particular region or area of the 3-D model may be targeted for a particular application, and a root-mean-squared (RMS) value of that region may be required to be as small as possible to optimize that region. As another example, the range threshold may bet set so that the 3-D model is optimized globally. In this example, the range may be optimized in order to find a global minimum in order to reduce the total error and optimize the total accuracy map globally.

There are various possible sources of uncertainty, inaccuracy, or error that are analyzed in generating the accuracy map. The different sources may be used to generate individual accuracy maps, which may be combined into a single accuracy map. The resulting accuracy map may be used as a quality measure for the fitting of the SSM to the X-ray(s). For example, if the accuracy map indicates that the 3-D model is not accurate enough for designing a device for use with the object being modeled, then the 3-D model may be rejected. Otherwise, the 3-D model may be accepted for use in the device design. The accuracy map may contain local information (at each point of the model), which may allow for optimization in certain areas of the resulting 3-D surface model.

Standard deviation $\sigma$ may be used to represent uncertainties, errors, accuracies, and inaccuracies relating to the accuracy maps. The standard deviation relates to standard deviations on vectors, and will be referred to as $\vec{\sigma}$.

The following formula may be used in the formation of accuracy maps and illustrates how a linear combination of a vector of independent, stochastic, normally distributed variables is distributed (also normally):

$$\left.\begin{array}{l} X \sim N(\mu_X, \sigma_X^2) \\ Y \sim N(\mu_Y, \sigma_Y^2) \\ Z = X + Y \end{array}\right\} \Rightarrow Z \sim N(\mu_X + \mu_Y, \sigma_X^2 + \sigma_Y^2)$$

Given a vector $\vec{x}$ with corresponding $\vec{\sigma}$ and a matrix P, the standard deviations of a transformed vector $P \cdot \vec{x}$ $\vec{\sigma}_t$ may be computed from:

$$\vec{\sigma}_t \circ \vec{\sigma}_t = (P \circ P) \cdot (\vec{\sigma} \circ \vec{\sigma})$$

Where the $\circ$ notation is a Hadamard product (element-wise multiplication). This equation may be used to generate each of the accuracy maps described below.

A first type of accuracy map may be based on inaccuracies caused by error in the input data. For example, 2-D input data (e.g., X-ray images) may have limited accuracy due to the nature of obtaining and measuring the data. This type of error may be referred to as propagated input error and results from the input itself. In some aspects, the contour information from X-rays may be used to determine the errors in the X-rays.

There is the error on the X-ray itself because the X-ray imaging device is a measuring device and there is a limit to its accuracy. The error or noise on the X-ray may result from blurring of the image, which may be caused by the processing software of the X-ray device or by X-ray distraction. In some aspects, the error may be caused by objects that are not intended to be captured by an X-ray imaging device that are introduced into the viewing field of the X-ray imaging device.

The input error is translated into a standard deviation vector on an input vector $\vec{m}_r$ of the X-ray that is used to fit a SSM on. A standard deviation may be defined for each coordinate of each individual input vector $\vec{m}_r$ to get a standard deviation vector $\vec{\sigma}_{Xray}$. To begin with, a global standard deviation over the complete X-ray of three times the pixel size may be used. In some aspects, it may be possible to indicate that the σ must be larger, which may be done by modifying the corresponding coordinates of $\vec{\sigma}_{Xray}$ (e.g., via a user interface).

Once the standard deviation vector $\vec{\sigma}_{Xray}$ is established, the standard deviations may then be propagated to the final shape vector $\vec{m}$. The standard deviations may be propagated to the final shape vector $\vec{m}$ using:

$$\vec{m} = \vec{m}_{av} + P \cdot \vec{k}_{ls} + (P \cdot V' \cdot V'') \cdot \vec{t}_{op}$$

And we obtain V″ by another SVD:

$$\Sigma^{-1/2} \cdot V'^t = U'' \cdot \Sigma'' \cdot V''^t$$

Where $\vec{k}_{ls}$ is the least squares solution, $\vec{m}$ is a shape vector, $\vec{m}_{av}$ is an average vector, P is the matrix containing the principal components, V' is a matrix including the columns of the matrix V that have a zero as an inverted singular value, and V″ is obtained through the SVD above. The least squares solution $\vec{k}_{ls}$ is calculated as:

$$\vec{k}_{ls} = V \cdot S^+ \cdot U^t \cdot (\vec{m}_r - \vec{v}_{ar})$$

So:

$$\vec{m} = \vec{m}_{av} + (P \cdot V \cdot S^+ \cdot U^t) \cdot (\vec{m}_r - \vec{v}_{ar}) + (P \cdot V' \cdot V'') \cdot \vec{t}_{op}$$

A new matrix may be defined as:

$$T_{ls} = P \cdot V \cdot S^+ \cdot U^t$$

The propagated input error ($\vec{\sigma}_{t1}$) accuracy map may then be computed from the error on the X-ray image using:

$$\vec{\sigma}_{t1} \circ \vec{\sigma}_{t1} = (T_{ls} \circ T_{ls}) \cdot (\vec{\sigma}_{Xray} \circ \vec{\sigma}_{Xray})$$

A second type of accuracy map may be based on inaccuracies caused by errors in fitting a simulated model relating to the physical object (e.g., the SSM) to the input data relating to the physical object (e.g., the X-ray image data). For example, errors may arise from misalignment of the SSM with the X-ray or by incompleteness of the SSM itself.

This type of error may be referred to as misfit error and is made up of the fitting residue. The SSM is fitted towards target contours on the X-ray, and the misfit error is a measure for how well this target was reached. The difference between the target contours and the silhouette curves of the fitted SSM described above make up the misfit error. The misfit error is different from the other types of error because it does not represent an uncertainty. The misfit error instead indicates how much the target is missed.

In some aspects, the fitting method may be implemented until the misfit error is of the same order of magnitude as the propagated input error, which is the error on the X-rays themselves before propagating them over the resulting 3-D model. It may not make sense to implement the fitting method to try for less error than the input error because this over fitting may lead to unstable results.

There may be different causes of the misfit error. In some aspects, the cause of the misfit error may be due to the SSM not containing a configuration that fits the one or more X-rays. For example, if there is not a possible fit using the SSM with a particular case, such as if the case is completely different from all cases in the training set, then the case may be rejected. As another example, the fit may include error in only a few isolated areas because the small details of a particular case are not considered in the SSM. The effect of this error on the resulting 3-D model (e.g., an STL) may be determined and analyzed in order to determine the error on the rest of the surface. In this example, the same formulas described above with regard to propagated input error may be used to propagate the misfit error that is in the isolated areas over the surface of the model, taking into account that the misfit error is a real error, not an uncertainty (as in propagated input error). Once the misfit error is propagated over the surface of the model, it is determined whether the SSM fits the particular case based on whether the error is large everywhere on the surface. A threshold error level may be used to determine a sufficient error for rejection of the case. In some aspects, the misfit error may be propagated using the formulas above in any case (e.g., if there is not a possible fit using the SSM), and it may be determined whether the error is large everywhere on the surface of the model in order to reject or accept the case.

In some aspects, the cause of the error may be due to a fitting algorithm not finding the correct solution. For example, an iterative optimization algorithm may be used as the fitting algorithm, as described above, and may end up in a local minimum or may stop too early. In these cases, the case may be rejected. In some aspects, the propagated input error formulas above may be used to determine whether the error over the entire surface of the 3-D model is too high in order to reject or accept the case.

In some aspects, in the event there is misfit error resulting in a SSM that may not be used in the fitting or there is an error in the fitting algorithm, the accuracy analysis may be stopped prior to generating the other types of accuracy maps and the case may be rejected.

A third type of accuracy map may be based on inaccuracies caused by lack of data in the input data. For example, 2-D input image data may not provide enough data to accurately portray each component of the physical object. This type of error may be referred to as insufficient data error.

As described above, instead of determining a least squares solution, the statistically most likely solution in a subspace of all best solutions may be determined using the high probability optimal fitting technique and may be used to map points on the SSM to identified points on an object. The statistically most likely solution may be selected from the subspace according to the statistical distribution within the SSM. There is uncertainty within this subspace. Similar to that described above with respect to the propagated input error, the following formulas for the fit may be used in the generation of the accuracy map based on the insufficient data error:

$$\vec{m} = \vec{m}_{av} + P \cdot \vec{k}_{op}$$
$$= \vec{m}_{av} + P \cdot (\vec{k}_{ls} + V' \cdot \vec{t}_{op})$$

In the case of insufficient data error, it may be determined with what standard deviations the coefficients of $\vec{t}_{op}$ are distributed. Once the standard deviations are determined for which the coefficients of $\vec{t}_{op}$ are distributed, the linearity may be used to calculate the standard deviations ($\sigma$) on the coefficients of the shape parameter $\vec{m}$.

To determine the standard deviations on $\vec{t}_{op}$, which may be referred to as $\vec{\sigma}_t$, the distribution function in the linear space of all least-squares solutions may be determined (see $g(\vec{t})$ equation above). Once it is determined that $\vec{t}_{op}$ is the peak of this function, the formula simplifies to:

$$g(\vec{t}) = \frac{1}{(2\pi)^{\frac{n}{2}}|\Sigma|^{\frac{1}{2}}} \exp\left(-\frac{1}{2}(\vec{k}_{op} + \vec{t})^T \cdot V'^T \cdot \Sigma^{-1} \cdot V' \cdot (\vec{k}_{op} + \vec{t})\right)$$

As noted above, $\Sigma' = (V'^T \cdot \Sigma^{-1} \cdot V')^{-1}$. This shorthand notation may be used in the above equation to get:

$$g(\vec{t}) = \frac{1}{(2\pi)^{\frac{n}{2}}|\Sigma|^{\frac{1}{2}}} \exp\left(-\frac{1}{2}(\vec{k}_{op} + \vec{t})^T \cdot \Sigma'^{-1} \cdot (\vec{k}_{op} + \vec{t})\right)$$

Based on this equation, $\vec{\sigma}_t$ is determined by $\Sigma'^{-1}$. The matrix $\Sigma'^{-1}$ is symmetrical and positive definite so it has orthogonal eigenvectors and strictly positive eigenvalues. Accordingly, $\Sigma'^{-1}$ is typically not a diagonal matrix. A transformation of the solution space (only k -dimensional) may be done to get statistically independent variables. For example, an eigendecomposition of $\Sigma'^{-1}$ may be calculated. Prior to performing the eigendecomposition of $\Sigma'^{-1}$, the construction of $\Sigma'^{-1}$ may be optimized. $\Sigma'^{-1}$ is represented by the following equation:

$$\Sigma'^{-1} = V'^T \cdot \Sigma^{-1} \cdot V'$$

Where $\Sigma^{-1}$ is the original (orthogonalised) matrix:

$$\Sigma^{-1} = \begin{pmatrix} \frac{1}{\sigma_1^2} & \cdots & 0 \\ \vdots & \ddots & \vdots \\ 0 & \cdots & \frac{1}{\sigma_n^2} \end{pmatrix} \Rightarrow \Sigma^{-\frac{1}{2}} = \begin{pmatrix} \frac{1}{\sigma_1} & \cdots & 0 \\ \vdots & \ddots & \vdots \\ 0 & \cdots & \frac{1}{\sigma_n} \end{pmatrix}$$

So:

$$(\Sigma^{-1/2} \cdot V')^T \cdot (\Sigma^{-1/2} \cdot V') = \Sigma'^{-1}$$

An SVD may then be calculated to obtain the eigendecomposition:

$$\Sigma^{-1/2} \cdot V' = U'' \cdot \Sigma'' \cdot V''^T$$

As a result, the following may be calculated:

$$\Sigma'^{-1} = \left(\Sigma^{-\frac{1}{2}} \cdot V'\right)^T \cdot \left(\Sigma^{-\frac{1}{2}} \cdot V'\right)$$
$$= V'' \cdot \Sigma'' \cdot U''^T \cdot U'' \cdot \Sigma'' \cdot V''^T$$
$$= V'' \cdot \Sigma''^2 \cdot V''^T$$

Accordingly, the standard deviations in the solution space is determined:

$$\Sigma''^2 = \begin{pmatrix} \frac{1}{\sigma''^2_1} & \cdots & 0 \\ \vdots & \ddots & \vdots \\ 0 & \cdots & \frac{1}{\sigma''^2_k} \end{pmatrix}$$

The $\sigma''$ represent the standard deviations on the vector $\vec{t}''$ where:

$$V'' \vec{t}'' = \vec{t}$$

The final result taking into account the above parameters is:

$$\vec{m} = \vec{m}_{av} + P \cdot (\vec{k}_{ls} + V' \cdot V'' \cdot \vec{t}'')$$
$$= \vec{m}_{av} + P \cdot \vec{k}_{ls} + (P \cdot V' \cdot V'') \cdot \vec{t}''$$

The standard deviations on the shape vector, which make up the insufficient data error accuracy map, that are to be determined may be referred to as $\vec{\sigma}_{t3}$. Based on the above functions, these standard deviations $\vec{\sigma}_{t3}$ may be calculated as:

$$\vec{\sigma}_{t3} \circ \vec{\sigma}_{t3} = ((P \cdot V' \cdot V'') \circ (P \cdot V' \cdot V'')) \cdot (\vec{\sigma}'' \circ \vec{\sigma}'')$$

A fourth type of accuracy map may be based on the incompleteness of the SSM itself. This type of error may be referred to as tail error. SSMs may grow very large, resulting in the number of components being cut off at a level before they become meaningless and impossible to fit. The resulting standard deviations may be very local. The tail error results from the tailing components that were cut off. Accordingly, the tail error accuracy map is the error of the part of the SSM that was disregarded in a condensed form.

The accuracy map based on the tail error may be created by considering the complete SSM, before the cutting off of the tailing components, and calculating the full vector of standard deviations $\vec{\sigma}_{SSM_{full}}$ of the complete SSM. The standard deviation of the tailing components $\vec{\sigma}_{SSM_{tail}}$ may be obtained by putting all standard deviations that correspond to components that are not thrown away to 0. The tail error may then be calculated using:

$$\vec{\sigma}_{t4} \circ \vec{\sigma}_{t4} = (P \circ P) \cdot (\vec{\sigma}_{SSM_{tail}} \circ \vec{\sigma}_{SSM_{tail}})$$

In some aspects, the tail error accuracy map may only need to be computed once for the SSM because it is independent of the fitting. The tail error accuracy map may thus be stored with the SSM.

A fifth type of accuracy map may be based on grey value gradients. For example, grey value gradients of the 3-D model of the physical object and/or the input image may be determined (e.g., using gradient maps) and may be used to detect edge information at particular points of the 3-D model and/or the input image. For example, gradient maps may be generated in order to represent edge and contour information in the 3-D model and/or the image. In some aspects, the intensity or steepness of the grey value gradients may be mapped onto the 3-D model to reflect how certain or accurate segmentation of the 3-D model will be. Higher intensities or steepness of grey value gradients at various points on the 3-D model correspond to more clearly defined boundaries between objects in the 3-D model at those points. For example, a large grey value gradient (e.g., a value of 500) value at a particular point on a 3-D model of a patient's leg may indicate a clearly defined boundary between the patient's bone and cartilage around the bone. As another example, a small grey value gradient (e.g., a value of 100) at a point on a 3-D model may indicate that an accurate segmentation at that point is unlikely. For each point on a 3-D model, a mapping may be created looking at the grey value gradients at each point. The resulting accuracy map may be used to indicate how certain or accurate the segmentation will be in different regions of the 3-D model.

Each of the accuracy map types may be created by mapping the resulting standard deviations representing inaccuracies, errors, uncertainties, etc. to the surface of the 3-D model of the physical object. In some aspects, the 3-D model surface may be divided into reliable and unreliable zones. In some aspects, as described above, the five types of accuracy maps may be combined into a single accuracy map used to determine the accuracy or reliability of each point on the 3-D model.

Returning to FIG. 5, the process 500 continues at block 508 to determine whether the 3-D model of the physical object satisfies an accuracy threshold based on the accuracy map or maps. The accuracy threshold may be set by a user or may correspond to requirements and/or constraints of the particular application for which the device design applies. The accuracy threshold may be set to determine whether the 3-D model of the physical object is sufficiently accurate for the particular application so as to proceed to the device design phase. For example, the accuracy of a 3-D model of a patient's femur may be analyzed to determine if the model is sufficiently accurate for use in the design of a device or tool that is to be used with the femur.

Satisfaction of the accuracy threshold may be determined using various methods. For example, the 3-D model with the one or more accuracy maps may be analyzed to determine whether too many inaccuracies are present in the 3-D model. In some aspects, each type of accuracy map may be analyzed individually to determine whether there are too many inaccuracies of any particular type. For example, if too much noise is present in the first type of accuracy map (e.g., due to external objects being included in the viewing field of an image capturing device) such that the reliability of the 3-D model is compromised, then the process may determine that the accuracy threshold has not been met. As another example, if a gradient value based accuracy map is used and too many points on the 3-D model include low gradient values, then the process may determine that the accuracy threshold has not been met because the 3-D model resulting from reconstruction of the image data is not accurate enough to proceed to the device design phase described below. In some aspects, the single accuracy map resulting from the combination of the different individual accuracy maps may be analyzed as a whole with respect to the 3-D model to determine whether too much error is present. For example, the combination of error found by combining the five types of accuracy maps may be quantified and compared with a base line threshold value to determine whether to continue with or reject the design case.

The process operates to reject the design case at block 512 in the event the 3-D model does not satisfy the accuracy threshold. If the 3-D model does satisfy the accuracy threshold, and it is thus determined that the 3-D model is sufficiently accurate for use in the device design, the process continues by generating a simulated representation of a device at block 510. The simulated representation represents a device that is designed to be used with the physical object. In some aspects, the device may include a surgical device (e.g., a surgical guide, an orthotic device, a prosthetic device, a surgical tool, etc.) that is designed to be used in surgery of a patient's bone, which is represented by the 3-D model. For example, a surgical guide or other medical or surgical device, tool, etc. may be designed and a model of the device may be generated to represent the designed device.

At block 514, the process determines whether to check the stability of the device design as represented by the simulated representation. The process skips to step 520 to determine whether to simulate a fit if the process determines not to check the stability of the device. If the process determines to check the stability, then the stability of the simulated representation of the device is determined at block 516. For example, stability of the device may be analyzed with respect to the contact surface of the physical object upon which the device will be used. The stability of the device design may be determined based on the simulated representation of the device and the 3-D model of the physical object. In some aspects, translational and rotational stability may be determined. For example, a surgical device, such as a surgical guide, may need to fit on a particular position on a patient's body and the fit of the device may need to be stable to prevent mistakes in surgery.

In some aspects, to determine the stability of the device design, one or more contact surfaces on the physical object may be determined based on the 3-D model of the physical object. The contact surfaces correspond to the portions of the device that will come into contact with the physical object. Based on the determined contact surfaces, stable positions of the device with respect to the contact surfaces may be determined and may be used in the device design. For example, geometric information of the contact surfaces, including vertex coordinates and unit outward normal vectors of the faces of the contact surfaces, may be determined and may be used to define a stiffness of the contact between the device and the physical object. The stiffness characterizes the resistance that the contact between the device and the physical object provides towards an externally applied force. Using points that define the contact surface and the corresponding unit outward normal vector at each point, a spatial stiffness matrix of the contact may be determined. The translational and rotational stiffness of the contact may then be determined using the eigenvalues of the matrix. A translational and rotational stability parameter may be determined based on target registration error. Based on these stability parameters, a stability score may be determined for the device design to provide a measure of the stability of the device design. The stability score also allows a comparison of different device designs with respect to the stability of each design.

At block 518, the process determines whether the simulated representation of the device satisfies a stability threshold. The stability threshold may be set to determine whether the simulated representation of the device is sufficiently stable for the particular application for which the device is to be used. The stability threshold may be set by a user or may be automatically set and may vary depending on the particular application. For example, the stability threshold may be used to determine whether a simulated surgical guide design is stable with respect to the contact surface of a body part for which the guide is being used. In some aspects, it is determined whether the simulated representation of the device satisfies the stability threshold based on the stability score. For example, the stability score of the device design may be determined and may be compared to a threshold level. If the stability score is above the threshold then the design is determined to be stable enough for use as an approved design, and the process may proceed to block 520. In some aspects, if the stability score is below the stability threshold, the device design may be rejected. The process may continue by generating a second simulated representation of the device, by returning to block 510, if the simulated representation of the device does not satisfy the stability threshold. The process may then determine whether the second simulated representation satisfies the stability threshold, for example by determining the stability score of the second device design. The process may continue to generate subsequent simulated representations of the device until one of the representations satisfies the stability threshold. For example, various device designs may be analyzed with respect to the stability of the device on the contact surface of a physical object upon which the device will be used. In some aspects, the stability of multiple device designs may be determined and the design with the highest stability score may be chosen as the approved design.

At block 520, the process continues by determining whether to simulate a fit of the device on the 3-D model of the physical object. The process may determine not to simulate the fit and may proceed to block 522 where the process may generate an approved design. If the process determines to simulate the fit, the process continues at block 524 by simulating a fit of the device on the 3-D model of the physical object. In some aspects, the process may simulate a fit of the device on one or more variations of the 3-D model of the physical object.

In some aspects, any of the fitting methods described above in FIGS. 6-7 may be used to fit the device on the 3-D model of the physical object. For example, an iterative closest point process may be used to simulate the fit of the device on the 3-D model. For example, the fit of the device to the 3-D model may be done by registering or aligning the simulated representation of the device with the 3-D model of the physical object. This may be accomplished by selecting points on the simulated representation of the device and/or the 3-D model and then matching the various data points on the simulated representation of the device with data points on the 3-D model. The points may be selected from the simulated representation of the device only, the 3-D model only, or from both the simulated representation of the device and the 3-D model. In some aspects, matching may be done by determining the nearest points on the 3-D model relative to given points on the simulated representation of the device. Further, various translations and rotations of the simulated representation of the device may be tested relative to the 3-D model in order to match corresponding points and align the simulated representation of the device and the 3-D model shape. The process may iteratively select and match points on the simulated representation of the device and the 3-D model in order to refine the fit simulation and minimize the distance between the points. By simulating the fit of the device on variations of the 3-D model, a best fit of the device with respect to the 3-D model may be determined. The variations of the 3-D model may be created using input from the accuracy maps. The output of the fit simulation includes a resulting position of the device on the physical object.

At block 526, the process determines whether the simulated fit of the device on the 3-D model of the physical object is within a tolerance threshold. As described above, the output of the fit simulation includes a position of the device on the object. The resulting position of the device on the object may then be compared to a planned position where the device was designed with respect to the bone. The difference between this planned position and the resulting position determined based the fit simulation is then compared to the tolerance threshold. The tolerance threshold is used to check whether the device will be used during its planned application within a bounded region of its planned position. In some aspects, comparing the fit simulation to the tolerance threshold may be used to check whether the designed device has only one unique position. In some aspects, comparing the fit simulation to the tolerance threshold may be used to check whether possible differences in various contact surfaces of the physical object during the particular application of the device (as predicted by the one or more accuracy map and caused by the uncertainties of the imaging and segmentation process) will have a large impact on the position of the device during the application. If the simulated fit is not within the tolerance threshold, the process proceeds to reject the design case regarding design of the device at block 512. At block 522, the method generates an approved design of the device if the simulated fit is within the tolerance threshold.

In some aspects, the processes described in FIGS. 4 and 5 may be used to design a surgical device (e.g., a surgical guide, surgical tool, orthotic, or a prosthetic) for use in surgery of a human body part. For example, the process may be used to design a surgical guide for use in surgery on a patient's femur. A 3-D model of the patient's femur may be generated at block 502. For example, the 3-D model may be generated using the fitting methods described above with an X-ray image of the patient's femur as input, by segmentation of 3-D image data (e.g., MRI or CT image data), by 3-D reconstruction of 3-D image data, etc. The accuracy of the 3-D model may be checked at blocks 504-508 using, for example, accuracy maps created at block 506. Further, a design for the surgical guide may be determined at block 510 and may be represented by a model (e.g., a 2-D or 3-D model). The surgical guide design may be checked for stability with regard to the patient's femur at blocks 514-518. A fit simulation may be done by registering or aligning the model of the surgical guide with a 3-D model of the patient's femur. Various data points on the surgical guide model and/or the 3-D model of the femur may be selected. The data points from the two models may then be matched. The fit of the surgical guide may be simulated on different variations of the 3-D model of the patient's femur. After the matching is complete, a best fit between the guide and the patient's femur is determined. A resulting position of the surgical guide on the patient's femur may then be determined based on the fit simulation. The resulting position of the surgical guide on the patient's femur may then be compared to a planned position that the guide was designed to be placed with respect to the bone. The difference between this planned position and the resulting position from the fit simulation may then be compared to a tolerance threshold to determine whether the guide will be used during the surgery within a bounded region of its planned position. The tolerance threshold may be used to check whether the designed guide has only one unique position or whether potential differences in various contact surfaces of the femur during the surgery will have a significant impact on the position of the guide during surgery. The potential differences in contact surfaces of the femur may be predicted by the one or more accuracy maps and caused by the uncertainties of the imaging and segmentation process. Based on the comparison with the tolerance threshold, the process may determine whether to proceed with the design of the surgical guide.

In some aspects, if the design of the device is approved (e.g., a user is satisfied with the design), a printer (e.g., output device 240) may be used to generate the device based on the approved design of the device. The device may then be used along with the physical object in the manner for which it was designed. For example, a surgical guide may be designed for use in surgery on a patient's ankle using the process 500, and may be printed for use in the actual surgery.

In some aspects, a fitting method according to the methods described above (e.g., step 402 of FIG. 4 and/or step 502 of FIG. 5) may be used to generate the 3-D model of the physical object from one or more images (e.g., X-rays) by utilizing a statistical shape model (SSM). The images may be generated by imaging techniques that provide 2-D images, such as X-rays, ultrasound, or fluoroscopy. The images may include at least a view from the coronal and sagittal plane of the subject's region of interest.

In some aspects, a method using SSMs to create a 3-D model may include obtaining one or more 2-D images from a subject's region of interest (step a) and determining from the image(s) the 2-D edges of at least part of the subject's region of interest (step b). For example, the obtained images may be taken and contour lines may be generated from the images. Various tools may be used for creating the edges, including manual edge detection or automatic tools such as the Canny edge detection algorithm, a Sobel edge detection algorithm, etc. The method may further include determining the position(s) of the imaging apparatus, allowing the method to determine the source point(s) of the imaging apparatus relative to the subject (step c). The method may further include providing a SSM based on the subject's region of interest (step d), and may alter the SSM at least once to align the SSM with the source point and the image(s) (step e). For example, the SSM may be analyzed together with the image(s), and various characteristics of the SSM may be adapted and manipulated (e.g., using a computer 102a). For example, after obtaining the SSM and prior to fitting the SSM with the image(s), the SSM may be manipulated or altered in order to provide adequate results during the fitting process, including changing the position and/or scaling of the SSM and changing the SSM parameters to align the SSM with the 2-D edges of at least part of the subject's region of interest. In some aspects, the alteration of the SSM may be done by changing the shape of the SSM, e.g. by changing the scale. In some aspects, altering the SSM may further include fitting the shape and/or the position of the SSM with the image(s), providing a shape fit of the SSM with the image(s). For example, a Z-position may be determined from the information about the source point. The fitting method may use this information to perform the scaling of the SSM, which may provide stable and reliable fitting results. In some aspects, a normalized SSM may be used.

The method may further include generating 2-D silhouette curves or points of the SSM computed from the source point(s) (step f) and may fit the 2-D silhouette curves or points with the 2-D edges of the image(s), thus generating fitted points and curves (step g). For example, after altering the SSM, 2-D silhouette curves or points of the SSM may be computed from the source point(s). The SSM may be projected onto a surface to generate an image similar to the actual images taken from the subject's region of interest. In some aspects, as described above with respect to FIG. 9, the silhouette curves or points generated from the SSM correspond to one or more points on the SSM for which the connecting line connecting said point with the source point is tangent to the SSM. In some aspects, corresponding point sets between the SSM and the 2-D images may be found. The silhouette curves or points on the SSM may correspond to the contour points on the 2-D image. For example, these points may be determined by finding zero-curves of the real-valued function g, as described above, by looking to a group of triangles and checking the corresponding configuration.

The method further includes back projecting the fitted points and curves to generate a 3-D silhouette (step h). For example, after generating the 2-D silhouette curves or points, the silhouette curves or points are fitted with the 2-D edges of the image(s) to generate fitted points and curves. The curves or points may be matched with the edges of the image(s), using, for example, a Symmetric Injective Nearest-neighbour (SIN) approach. The SIN approach includes a defined relation between the two sets of points. The relation includes point pairs where the first point comes from a first set (set 1) and the second point comes from a second set (set 2). A relation may exist between the first and second points when the first point is the closest point in set 1 to the second point and the second point is the closest point in set 2 to the first point. The result is a set of correspondences between the projected silhouette points and the 2-D image edges. The correspondences are back projected onto the original position of the SSM to generate a 3-D silhouette. As described above, the back projecting is performed by creating a correspondence between points of the SSM and a set of 3-D points using the information regarding the imaging source point. Accordingly, a 3-D model of the subject's region of interest may be generated.

The method may further include altering the SSM to align the SSM with the 3-D silhouette (step i) and may generate from the aligned SSM a 3-D model of the subject's region of interest (step j). For example, the SSM may be altered and aligned with the 3-D silhouette to provide an aligned SSM that is more accurate and of a higher quality than if unaligned. The 3-D model of the subject's region of interest may then be generated from the aligned SSM. Use of altered models to provide a more accurate and higher quality fitting may also be performed with respect to the fitting methods described above using SSMs.

The method may further include assessing the quality of the aligned SSM prior to generating the 3-D model, and optionally repeating steps f through i with the aligned SSM until the aligned SSM provides the required quality. For example, prior to the generation of the 3-D model, the aligned SSM may be further subjected to a number of iterative steps including generating 2-D silhouette curves or points of the aligned SSM, fitting the 2-D silhouette curves or points with the 2-D edges of said image(s), back projecting the fitted points and curves to generate a 3-D silhouette, altering the previously aligned SSM to re-align the SSM with the 3-D silhouette, and generating an improved aligned SSM. This process may be repeated several times resulting in a 3-D model fulfilling the requirements of quality, accuracy, and correctness that are required.

In some aspects, the fitting step (step g) may include a least-squares fitting. In some aspects, the fitting step may include the high probability optimal solution fitting technique described above. In some aspects, the 2-D contour points or lines of the images are determined based on the areas of the images that provide the highest degree of accuracy.

In some aspects, the method using an SSM further includes determining a measure of accuracy, uncertainty, and/or error attritibutable to the image quality. For example, as described above, an accuracy analysis may be conducted by analyzing sources of error. For example, one or more accuracy maps may be generated as described above. The accuracy maps may provide visual feedback of the accuracy, uncertainty, and/or error in a user interface.

In one example of the method using a SSM to generate a 3-D model, X-rays may be taken from healthy knee together with a ball bar. The ball bar may also be used to identify the Z-position of a knee on the X-ray machine. The dimensions of the ball bar may be measured (e.g., 218.02 mm) and the ball bar may be positioned in the middle (Z-position) of the patient's femur. Edge detection may be performed on the X-ray images using Canny edge detection (e.g., using Matlab) and/or manual edge detection to obtain a resulting contour image. A SSM may be selected and an initial position, scale, and/or shape may be provided. An average SSM (all factors to zero) may provide a good starting value for the shape parameters.

A calibration device may then be used to determine the correct position relative to the imaging apparatus, such a calibration device similar to that described above and described in, for example, PCT/EP2012/058242 (which is incorporated herein by reference in its entirety). As another example, the ball bar described above may be used to determine the correct position. For example, a distance between the two balls on the ball bar is 218.02 mm, the distance between the centers of the balls on the X-ray is 262.805 mm, and the Z-position of the source above the photographic plate is 1150 mm. In this example, the Z-position is at 195.974 mm. This Z-position may be used for the SSM, and the X/Y position and the orientation of the SSM are determined as well. The resulting SSM image may then be projected onto the 2-D contour images.

The contour images of the SSM and the X-ray image(s) are fitted with each other through a number of iterate steps (e.g., using least-squares fitting, the high probability optimal solution fitting technique, etc.) to generate a 3-D model of the knee. The projected images of the 3-D model result in contour curves that align closely to the original X-ray images.

In order to check the results, the healthy knee may also be scanned using a CT or MRI imaging device to generate a true 3-D image of the knee. The fitted 3-D model using the method described above may then be compared to the 3-D image of the CT or MRI scan (e.g., using a comparison analysis in 3-matic).

In some aspects, the images obtained and used in the fitting methods described above may include at least a view from the coronal and sagittal plane of the subject's region of interest. The sagittal plane is the vertical plane which passes from front to rear dividing the body into right and left sections and the coronal plane is any vertical plane that divides the body into ventral and dorsal (belly and back) sections. In some aspects, the methods described above may be performed based on only one single image. In some aspects, the use of two or more images may be used and may provide more accurate results.

In some aspects, the models used in the fitting methods described above may be aligned with the images by minimizing the amount of information available. For example, the amount of information may be minimized by first taking a virtual X-ray of the model (e.g., the SSM). This virtual X-ray may then be superimposed over an actual X-ray image of the area of interest. Once the virtual X-ray is superimposed over the actual X-ray, information between the virtual X-ray and real X-ray that does not overlap may be eliminated, providing an additional method for determining a more accurate fit between the model and the images. The accuracy of the alignment may also be indicated by the amount of overlapping information.

In some aspects, the resulting data provided by the accuracy maps and stability analysis described above may be used to physically alter or adjust the designed device prior to manufacturing the guide. For example, if an area of a device is not accurate based on the accuracy map, one or more objects (e.g., a cushioning element or device, a spring, etc.) may be added to vary the stiffness, size, shape, etc. of the device. In some aspects, cushioning devices may be added to the device, such as the cushioning device described, for example, in U.S. 2010/0161076 A1, the entire disclosure of which is incorporated herein by reference in its entirety. The addition of the one or more objects may compensate for the lack of accuracy and may provide a device that uniquely fits the physical object for which the device is designed and is rotationally and translationally stable.

As one example, a system of springs may be added to the device design and the spring strength may be modulated as a function of the stability, accuracy, error, and/or uncertainty. For locations on the device design that include an indication of good quality (e.g., stable and accurate), a surface spring may be attached that can be bended flush with the interfacing surface. For locations that include an indication of poor quality (e.g., unstable and/or inaccurate), a surface spring protruding more outward may be attached to the interfacing surface. As a result, a device may be designed that includes an adaptive surface that is able to accommodate potential errors in the geometrical reconstruction.

As another example, the surface roughness of a device may be modulated by including linear grooves that are perpendicular to the direction of least translational stability. The groove height may be modulated as a function of the translational stability of the portion of the device. By adding modulated grooves, the friction is increased locally in areas with less translational stability and the translational stability of these areas is increased.

Figures 12A, 12B:
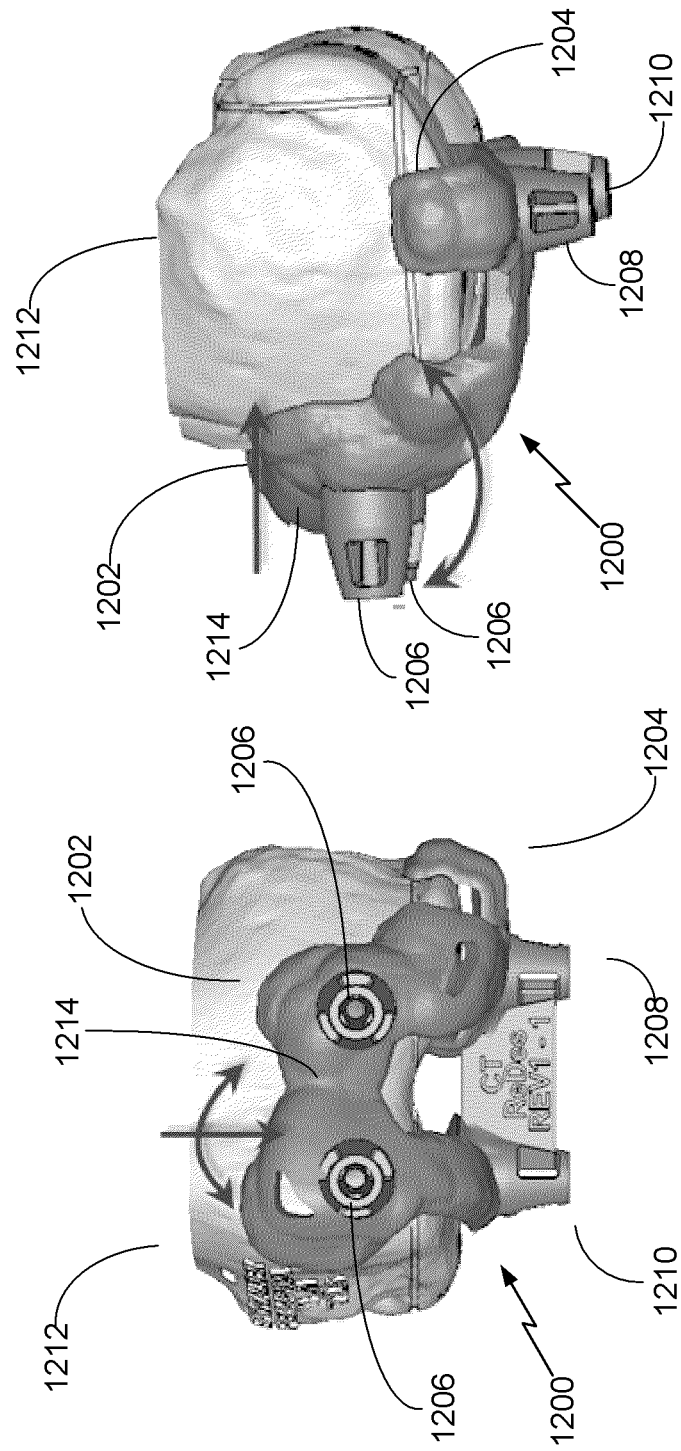
FIGS. 12a-12b illustrates an example of a surgical guiding tool.

FIGS. 12a and 12b illustrate an example of a surgical guiding tool 1200 that may be designed according to the processes of FIGS. 4 and 5. In some embodiments, the surgical guiding tool 1200 may be a femoral surgical guiding tool for a distal end of a femur 1212. While the description herein may describe a femur 1212 as an example of the bone, one of skill in the art will understand that a surgical guiding tool may be designed for use in surgery of other bones, such as the humerus, scapula, tibia, fibula, talus, spine, and other shoulder, hip, ankle, and/or finger bones. The surgical guiding tool 1200 includes a body 1202 that is configured to attach to at least one region or portion of the femur 1212. The body 1202 includes a first portion 1214, such as an anterior portion, that is configured to attach and secure the surgical guiding tool to an anterior region of the femur 1212. For example, the first portion 1214 may be configured to secure the surgical guiding tool 1200 to the bone and thus restrict undesired movement of the surgical guiding tool 1200. A clamp 1204 may also be used to secure the surgical guiding tool 1200 to the femur 1212. The secure attachment of the clamp 1204 to the bone ensures that the surgical guiding tool 1200 remains in a stable and secure position during surgery. The body 1202 of the surgical guiding tool 1200 may further include more than one clamp that is similar to clamp 1204. The use of a second clamp may add further stability of the surgical guiding tool 1200 to the femur 1212. The use of the first portion 1214 along with one or more clamps, such as clamp 1204, ensures that the surgical guiding tool remains secured to the femur 1212. By securing the surgical guiding tool 1200 in a stable manner, the surgical guiding tool may be securely and accurately placed on the bone so that surgery may be performed more accurately and safely due to little or no movement of the guide. For example, by attaching the first portion 1214 to the anterior region of the femur 1212 (e.g., to an osteophyte), and further attaching one or more clamps, such as clamp 1204, to one or more condyles, the surgical guiding tool 1200 will be restricted from various translational and rotational movements (e.g., posterior and anterior sliding, distal and proximal sliding, mediolateral sliding, internal-external rotation, varus-valgus movements, and/or flexion-extension).

The surgical guiding tool 1200 further includes apertures 1206, 1208, and 1210, which may aligned with areas of the femur 1212 corresponding to locations that need to be accessed for surgery, such as locations where holes are to be drilled. For example, portions of the bone where holes need to be drilled may be aligned with the apertures 1206. The holes may be created using a surgical tool device inserted into the apertures 1206, such as a drill, bur, saw, jig saw, lateral drill or any other cutting, milling or drilling instrument. The apertures 1206, 1208, and 1210 are positioned so that a surgical tool device that is passed through one or more of the apertures 1206, 1208, and 1210 can reach the bone at the desired location. The apertures 1206, 1208, and 1210 may be positioned in any direction relative to the bone as long as it provides access for a surgical tool device to reach the bone at the desired location. In some embodiments, the apertures 1206, 1208, and 1210 may protrude from the surface of the body 1214, as illustrated in FIGS. 12a and 12b. In some embodiments, the apertures may include safety stops to prevent a surgical tool device from advancing beyond a planned or determined depth into the bone. While the description herein may describe apertures 1206, 1208, and 1210 located at specific locations, one of skill in the art will understand that the content of the present application applies equally to aperture locations relating to patient-specific locations on different type of bones, and may be determined using pre-operative procedures described above. Further, the orientation and position of the apertures may correspond to pre-operative planning and procedures.

Using the processes described above in FIGS. 4 and 5, a surgical guiding tool, such as the guiding tool 1200, may be designed that is accurately customized to a specific patient's bone for a particular surgery and that is stable and secure to prevent movement during surgery.

In some embodiments, the devices described above may be partially or completely made by additive manufacturing, which allows efficient integration of patient-specific components that further increase the accuracy of the guiding tools. The patient-specific components of surgical device, for example, may be designed based on patient-specific parts of a particular body part (e.g., bone) of a patient. The patient specific components of the surgical guiding tools may be made by generating portions that are complementary to the patient-specific parts of the bone. For converting digital image information of the bone into a basic model, template, or mold that at least in part shows the positive or negative form of at least a portion of the bone, any suitable technique known in the art may be used, such as for example a rapid prototyping technique.

Rapid Prototyping and Manufacturing (RP&M) may be defined as a group of techniques used to quickly fabricate a scale model of an object typically using three-dimensional (3-D) computer aided design (CAD) data of the object. Currently, a multitude of Rapid Prototyping techniques are available, including stereo lithography (SLA), Selective Laser Sintering (SLS), Fused Deposition Modeling (FDM), foil-based techniques, etc.

A common feature of these techniques is that objects are typically built layer by layer. Stereo lithography, presently the most common RP&M technique, utilizes a vat of liquid photopolymer "resin" to build an object a layer at a time. On each layer, an electromagnetic ray, e.g. one or several laser beams which are computer-controlled, traces a specific pattern on the surface of the liquid resin that is defined by the two-dimensional cross-sections of the object to be formed. Exposure to the electromagnetic ray cures, or, solidifies the pattern traced on the resin and adheres it to the layer below. After a coat had been polymerized, the platform descends by a single layer thickness and a subsequent layer pattern is traced, adhering to the previous layer. A complete 3-D object is formed by this process.

Selective laser sintering (SLS) uses a high power laser or another focused heat source to sinter or weld small particles of plastic, metal, or ceramic powders into a mass representing the 3-dimensional object to be formed.

Fused deposition modeling (FDM) and related techniques make use of a temporary transition from a solid material to a liquid state, usually due to heating. The material is driven through an extrusion nozzle in a controlled way and deposited in the required place as described, for example, in U.S. Pat. No. 5,141,680, the entire disclosure of which is hereby incorporated by reference in its entirety.

Foil-based techniques fix coats to one another by means of gluing or photo polymerization or other techniques and cut the object from these coats or polymerize the object. Such a technique is described in, for example, U.S. Pat. No. 5,192,539, also incorporated herein by reference in its entirety.

Typically RP&M techniques start from a digital representation of the 3-D object to be formed. Generally, the digital is sliced into a series of cross-sectional layers which can be overlaid to form the object as a whole. The RP&M apparatus uses this data for building the object on a layer-by-layer basic. The cross-sectional data representing the layer data of the 3-D object may be generated using a computer system and computer aided design and manufacturing (CAD/CAM) software.

A selective laser sintering (SLS) apparatus may be used for the manufacture of a surgical guiding tool template instead of a computer model. It should be understood however, that various types of rapid manufacturing and tooling may be used for accurately fabricating these surgical templates including, but not limited to, stereolithography (SLA), Fused Deposition Modeling (FDM) or milling.

The subject-matter of this disclosure is operational with numerous general purpose or special purpose computing system environments or configurations. Examples of well-known computing systems, environments, and/or configurations that may be suitable for use with the invention include, but are not limited to, personal computers, server computers, hand-held or laptop devices, multiprocessor systems, microprocessor-based systems, programmable consumer electronics, network PCs, minicomputers, mainframe computers, distributed computing environments that include any of the above systems or devices, and the like.

As used herein, instructions refer to computer-implemented steps for processing information in the system. Instructions can be implemented in software, firmware or hardware and include any type of programmed step undertaken by components of the system.

If implemented in software, the functions described above may be stored on or transmitted over as one or more instructions or code on a computer-readable medium. The steps of a method or algorithm disclosed herein may be implemented in a processor-executable software module which may reside on a computer-readable medium. Computer-readable media includes both computer storage media and communication media including any medium that can be enabled to transfer a computer program from one place to another. A storage media may be any available media that may be accessed by a computer. By way of example, and not limitation, such computer-readable media may include RAM, ROM, EEPROM, CD-ROM or other optical disk storage, magnetic disk storage or other magnetic storage devices, or any other medium that may be used to store desired program code in the form of instructions or data structures and that may be accessed by a computer. Also, any connection can be properly termed a computer-readable medium. Disk and disc, as used herein, includes compact disc (CD), laser disc, optical disc, digital versatile disc (DVD), floppy disk, and blu-ray disc where disks usually reproduce data magnetically, while discs reproduce data optically with lasers. Combinations of the above should also be included within the scope of computer-readable media. Additionally, the operations of a method or algorithm may reside as one or any combination or set of codes and instructions on a machine readable medium and computer-readable medium, which may be incorporated into a computer program product.

A person/one having ordinary skill in the art would further appreciate that any of the various illustrative logical blocks, modules, processors, means, circuits, and algorithm steps described in connection with the aspects disclosed herein may be implemented as electronic hardware (e.g., a digital implementation, an analog implementation, or a combination of the two, which may be designed using source coding or some other technique), various forms of program or design code incorporating instructions (which may be referred to herein, for convenience, as "software" or a "software module), or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present disclosure.

A microprocessor may be any conventional general purpose single- or multi-chip microprocessor such as a Pentium® processor, a Pentium® Pro processor, a 8051 processor, a MIPS® processor, a Power PC® processor, or an Alpha® processor. In addition, the microprocessor may be any conventional special purpose microprocessor such as a digital signal processor or a graphics processor. The microprocessor typically has conventional address lines, conventional data lines, and one or more conventional control lines.

The systems described above may be comprised of various modules as discussed in detail. As can be appreciated by one of ordinary skill in the art, each of the modules may comprise various hardware components, sub-routines, procedures, definitional statements, and macros. Each of the modules may be separately compiled and linked into a single executable program and the description of each of these modules is used for convenience to describe the functionality of the preferred system. Thus, any processes that are undergone by each of the modules may be arbitrarily redistributed to one of the other modules, combined together in a single module, or made available in, for example, a shareable dynamic link library.

The systems described above may be used in connection with various operating systems such as Linux®, UNIX® or Microsoft Windows®.

The systems described above may be written in any conventional programming language such as C, C++, BASIC, Pascal, or Java, and ran under a conventional operating system. C, C++, BASIC, Pascal, Java, and FORTRAN are industry standard programming languages for which many commercial compilers can be used to create executable code. The system may also be written using interpreted languages such as Perl, Python or Ruby.

A web browser comprising a web browser user interface may be used to display information (such as textual and graphical information) to a user. The web browser may comprise any type of visual display capable of displaying information received via a network. Examples of web browsers include Microsoft's Internet Explorer browser, Netscape's Navigator browser, Mozilla's Firefox browser, PalmSource's Web Browser, Apple's Safari, or any other browsing or other application software capable of communicating with a network.

The subject-matter disclosed herein may be implemented as a method, apparatus or article of manufacture using standard programming or engineering techniques to produce software, firmware, hardware, or any combination thereof. The term "article of manufacture" as used herein refers to code or logic implemented in hardware or non-transitory computer readable media such as optical storage devices, and volatile or non-volatile memory devices or transitory computer readable media such as signals, carrier waves, etc. Such hardware may include, but is not limited to, field programmable gate arrays (FPGAs), application-specific integrated circuits (ASICs), complex programmable logic devices (CPLDs), programmable logic arrays (PLAs), microprocessors, or other similar processing devices.

Various modifications to the implementations described in this disclosure may be readily apparent to those skilled in the art, and the generic principles defined herein may be applied to other implementations without departing from the spirit or scope of this disclosure. Thus, the disclosure is not intended to be limited to the implementations shown herein, but is to be accorded the widest scope consistent with the claims, the principles and the novel features disclosed herein. The word "exemplary" is used exclusively herein to mean "serving as an example, instance, or illustration." Any implementation described herein as "exemplary" is not necessarily to be construed as preferred or advantageous over other implementations.

Certain features that are described in this specification in the context of separate implementations also can be implemented in combination in a single implementation. Conversely, various features that are described in the context of a single implementation also can be implemented in multiple implementations separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems can generally be integrated together in a single software product or packaged into multiple software products. Additionally, other implementations are within the scope of the following claims. In some cases, the actions recited in the claims can be performed in a different order and still achieve desirable results.

What is claimed is:

1. An apparatus for designing a device, the apparatus comprising:
    a processor configured to:
        generate a three-dimensional model of a physical object;
        determine whether the three-dimensional model satisfies an accuracy threshold based on an accuracy map, wherein the accuracy map comprises a confidence interval associated with each point in the accuracy map;
        generate a simulated representation of the device;
        determine whether the simulated representation of the device satisfies a stability threshold based on a stability score comprising:
            determining one or more contact surface between the simulated representation of the device and the three-dimensional model; and
            defining a stiffness of contact between the simulated representation of the device on the three-dimensional model at the one or more contact surfaces, wherein the stiffness of contact characterizes resistance that contact, between the simulated representation of the device and the three-dimensional model provides toward an externally applied force based on geometry of the one or more contact surfaces, wherein the stability score indicates a measure of stability based on the stiffness of contact;
        simulate a fit of the generated simulated representation of the device on the three-dimensional model if the simulated representation of the device satisfies the stability threshold to output a position and orientation of the generated simulated representation of the device on top of the three-dimensional model when the generated simulated representation of the device contacts the three-dimensional model comprising:
            registering or aligning the generated simulated representation of the device with the three-dimensional model so a number of data points on the generated simulated representation of the device match with a corresponding set of data points on the three-dimensional model;
        compare the position and orientation of the generated simulated representation of the device on the three-dimensional mode based on the simulated fit to a planned position and orientation of the device with respect to the physical object;
        determine whether the difference between the position and orientation of the generated simulated representation of the device on top of the three-dimensional model based on the simulated fit and the planned position and orientation of the device with respect to the physical object when the device contacts the physical object is within a tolerance threshold indicating whether the position and orientation of the generated simulated representation of the device are within a threshold with respect to the three-dimensional model; and
        generate an approved design of the device if the difference is within the tolerance threshold;
    an additive manufacturing device configured to:
        manufacture the approved design of the device.

2. The apparatus of claim 1, wherein the processor is configured to at least one of generate the accuracy map or retrieve the accuracy map from a memory.

3. The apparatus of claim 1, wherein the processor is configured to at least one of generate the stability score or retrieve the stability score from a memory.

4. The apparatus of claim 1, wherein the processor is configured to generate a second simulated representation of the device if the simulated representation of the device does not satisfy the stability threshold.

5. The apparatus of claim 1, wherein simulating a fit of the generated simulated representation of the device on the three-dimensional model includes simulating a fit of the generated simulated representation of the device on one or more variations of the three-dimensional model.

6. The apparatus of claim 5, wherein simulating a fit of the generated simulated representation of the device on the three-dimensional model includes registering the simulated representation of the device on top of the physical object to determine a best fit.

7. The apparatus of claim 1, wherein the device comprises a surgical device.

8. The apparatus of claim 7, wherein the surgical device includes at least one of a surgical guide, an orthotic device, a prosthetic device, and a surgical tool.

9. The apparatus of claim 7, wherein the physical object comprises a human body part.

10. The apparatus of claim 9, wherein simulating a fit of the generated simulated representation of the device on the three-dimensional model includes simulating a fit of a generated simulated representation of the surgical device on one or more variations of the three-dimensional model of the human body part.

11. The apparatus of claim 1, further comprising a printer configured to generate the device based on the approved design of the device.

12. The apparatus of claim 1, wherein the accuracy map is based on at least one of an error related to a 2D image of the physical object used to generate the three-dimensional model of the physical object or an error in a statistical shape model of the three-dimensional model.

13. The apparatus of claim 1, wherein registering or aligning the generated simulated representation of the device with the three-dimensional model comprises matching the number of data points on the simulated representation of the device to the corresponding set of data points on the three-dimensional model by determining one or more nearest points on the three-dimensional model relative to points on the simulated representation of the device.

14. A method of designing a device, the method comprising:
    generating a three-dimensional model of a physical object;
    determining whether the three-dimensional model satisfies an accuracy threshold based on an accuracy map, wherein the accuracy map comprises a confidence interval associated with each point in the accuracy map;
generating a simulated representation of the device;
determining whether the simulated representation of the device satisfies a stability threshold based on a stability score comprising:
  determining one or more contact surface between the simulated representation of the device and the three-dimensional model; and
  defining a stiffness of contact between the simulated representation of the device and the three-dimensional model at the one or more contact surfaces, wherein the stiffness of contact characterizes resistance that contact between the simulated representation of the device and the three-dimensional model provides toward an externally applied force based on geometry of the one or more contact surfaces, wherein the stability score indicates a measure of stability based on the stiffness of contact;
simulating a fit of the generated simulated representation of the device on the three-dimensional model if the simulated representation of the device satisfies the stability threshold to output a position and orientation of the generated simulated representation of the device on top of the three-dimensional model when the generated simulated representation of the device contacts the three-dimensional model comprising:
  registering or aligning the generated simulated representation of the device with the three dimensional model so a number of data points on the generated simulated representation of the device match with a corresponding set of data points on the three-dimensional model;
comparing the position and orientation of the generated simulated representation of the device on the three-dimensional model based on the simulated fit to a planned position and orientation of the device with respect to the physical object;
determining whether the difference between the position and orientation of the generated simulated representation of the device on top of the three-dimensional model based on the simulated fit and the planned position and orientation of the device with respect to the physical object when the device contacts the physical object is within a tolerance threshold indicating whether the position and orientation of the generated simulated representation of the device are within a threshold with respect to the three-dimensional model; and
generate an approved design of the device if the difference is within the tolerance threshold; and manufacture the approved design of the device using additive manufacturing.

15. The method of claim 14, further comprising at least one of generating the accuracy map or retrieving the accuracy map from a memory.

16. The method of claim 14, further comprising at least one of generating the stability score or retrieving the stability score from a memory.

17. The method of claim 14, further comprising generating a second simulated representation of the device if the simulated representation of the device does not satisfy the stability threshold.

18. The method of claim 14, wherein simulating a fit of the generated simulated representation of the device on the three-dimensional model includes simulating a fit of the generated simulated representation of the device on one or more variations of the three-dimensional model.

19. The method of claim 18, wherein simulating a fit of the generated simulated representation of the device on the three-dimensional model includes registering the simulated representation of the device on top of the physical object to determine a best fit.

20. The method of claim 14, wherein the device comprises a surgical device.

21. The method of claim 20, wherein the surgical device includes at least one of a surgical guide, an orthotic device, a prosthetic device, and a surgical tool.

22. The method of claim 20, wherein the physical object comprises a human body part.

23. The method of claim 22, wherein simulating a fit of the generated simulated representation of the device on the three-dimensional model includes simulating a fit of a generated simulated representation of the surgical device on one or more variations of the three-dimensional model of the human body part.

24. The method of claim 14, further comprising printing the device based on the approved design of the device.

25. The method of claim 14, wherein the accuracy map is based on at least one of an error related to a 2D image of the physical object used to generate the three-dimensional model of the physical object or an error in a statistical shape model of the three-dimensional model.

26. The method of claim 14, wherein registering or aligning the generated simulated representation of the device with the three-dimensional model comprises matching the number of data points on the simulated representation of the device to the corresponding set of data points on the three-dimensional model by determining one or more nearest points on the three-dimensional model relative to points on the simulated representation of the device.

* * * * *